United States Patent
Subramaniam et al.

(10) Patent No.: US 6,207,375 B1
(45) Date of Patent: Mar. 27, 2001

(54) TGF-β INDUCIBLE EARLY FACTOR-1 (TIEF-1) AND A METHOD TO DETECT BREAST CANCER

(75) Inventors: Malayannan Subramaniam, Zumbrota; Thomas C. Spelsberg; Patrick C. Roche, both of Rochester, all of MN (US)

(73) Assignee: Mayo Foundation for Medical Educational & Research, Rochester, MN (US)

( * ) Notice: Subject to any disclaimer, the term of this patent is extended or adjusted under 35 U.S.C. 154(b) by 0 days.

(21) Appl. No.: 09/077,991

(22) PCT Filed: Dec. 11, 1996

(86) PCT No.: PCT/US96/19555

§ 371 Date: Jul. 7, 1998

§ 102(e) Date: Jul. 7, 1998

(87) PCT Pub. No.: WO97/21810

PCT Pub. Date: Jun. 19, 1997

(51) Int. Cl.[7] .................................................. C12Q 1/68
(52) U.S. Cl. .......................... 435/6; 435/91.1; 435/91.2; 435/69.1; 536/23.5; 530/399
(58) Field of Search .............................. 435/6, 91.1, 91.2, 435/69.1; 536/23.5; 530/399

(56) References Cited

PUBLICATIONS

Arnoletti, J.P., et al., "Thrombospondin and Transforming Growth Factor–Beta 1 Increase Expression of Urokinase-–type Plasminogen Activator and Plasminogen Activator Inhibitor–1 in Human MDA–MB–231 Breast Cancer Cells", *Cancer*, 76 (6), pp. 998–1005, (Sep. 15, 1995).

Blok, L.J., et al., "Characterization of an early growth response gene, which encodes a zinc finger transcription factor, potentially involved in cell cycle regulation", *Molecular Endocrinology*, 9 (11), pp. 1610–1620, (Nov. 1995).

DuBois, R.N., et al., "Transforming growth factor α Regulation of two zinc finger–containing immediate early response genes in intestine", *Cell Growth and Differentiation*, 6, pp. 523–529, (May 1995).

Hagen, G., et al., "Cloning by Recognition Site Screening of Two Novel GT Box Binding Proteins: A Family of Sp1 Related Genes", *Nucleic Acids Research*, 20 (21), pp. 5519–5525, (Nov. 11, 1992).

Kadonaga, J.T., et al., "Isolation of cDNA Encoding Transcription Factor Sp1 and Functional Analysis of the DNA Binding Domain", *Cell*, 51, pp. 1079–1090, (Dec. 24, 1987).

Lafon, C., et al., "Early gene responses associated with transforming growth factor–β1 growth inhibition and autoinduction in MCF-7 breast adenocarcinoma cells", *Biochimica et Biophysica Acta*, 1266 (3), Molecular cell research, pp. 288–295, (1995).

Liu, C., et al., "EGR–1, the reluctant suppression factor", *Critical Reviews in Oncogenesis*, 7 (1/2), pp. 101–125, (1996).

Subrumaniam, M., et al., "Characterization of a TGF–β Regulated Gene Encoding a Putative Zinc Finger Protein and SRC Substrate in Human Osteoblasts", *Journal of Bone Mineral Research*, 10 (S1), Abstract No. 21, p. S144, (Sep. 1995).

Shibanuma, M., et al., "Characterization of the TGF β1–inducible hic–5 gene that encodes a putative novel zinc finger protein and its possible involvement in cellular senescence", *Journal of Biological Chemistry*, 269 (43), pp. 26767–26774, (Oct. 28, 1994).

Shibanuma, M., et al., "Isolation of a Gene Encoding a Putative Leucine Zipper Structure that is induced by transforming growth factor β1 and Other Growth Factors", *Journal of Biological Chemistry*, 267 (15), pp. 10219–10224, (May 25, 1992).

Snyder, R., et al., "Cellular and molecular correlates in human breast tumor progression", *Proceedings of the American Association for Cancer Research*, 36, Abstract No. 48, Toronto, Ontario, Canada, p. 8, (Mar. 18–22, 1995).

Subramaniam, M., et al., "Identification of a novel TGF–β Regulated Gene Encoding A Putative Zinc finger Protein in human steoblasts", *Nucleic Acids Research*, 23 (23); pp. 4907–4912, (Aug. 1994).

Subramaniam, M., et al., "Identification of a Novel TGF–β Inducible Early Gene in Human Osteoblasts", *Journal of Bone Mineral Research*, 9 (S1), Abstract No. 81, p. S141, (Aug. 1994).

Takenaka, I.M., et al., "Transforming growth factor–β1 rapidly induces Hsp70 and Hsp90 Molecular Chaperones in Cultured Chicken Embryo Cells", *Journal of Cellular Physiology*, 152 (3), pp. 568–577, (Sep. 1992).

Tau, K.R., et al., "Estrogen Upregulation of a Novel Transforming Growth Factor–β Inducible Gene in a Human Osteoblastic Cell Line", *Journal of Bone Mineral Research*, 10 (S1), Abstract No. T547, p. S491, (Sep. 1995).

*Primary Examiner*—W. Gary Jones
*Assistant Examiner*—Janell E. Taylor
(74) *Attorney, Agent, or Firm*—Schwegman, Lundberg, Woessner & Kluth, P.A.

(57) ABSTRACT

Methods to determine TIEF-1 polypeptide, or genetic rearrangements in the TIEF-1 gene, in a sample are provided. Also provided are TIEF-1 specific antibodies and nucleic acid probes, and methods of employing those antibodies and probes to detect breast cancer in situ in a mammalian tissue sample.

9 Claims, 5 Drawing Sheets

```
   1 GAATTCGGCACGAGCGCCCGTCTGTGGCCAAGCAGCCAGCAGCCTAGCAGCCAGTCAGCT
  61 TGCCGCCGGCGGCCAAGCAGCCAACCATGCTCAACTTCGGTGCCTCTCTCCAGCAGACTG
                         M   L   N   F   G   A   S   L   Q   Q   T   A    12
 121 CGGAGGAAAGAATGGAAATGATTTCTGAAAGGCCAAAAGAGAGTATGTATTCCTGGAACA
      E   E   R   M   E   M   I   S   E   R   P   K   E   S   M   Y   S   W   N   K    32
 181 AAACTGCAGAGAAAAGTGATTTTGAAGCTGTAGAAGCACTTATGTCAATGAGCTGCAGTT
      T   A   E   K   S   D   F   E   A   V   E   A   L   M   S   M   S   C   S   W    52
 241 GGAAGTCTGATTTTAAGAAATACGTTGAAAACAGACCTGTTACACCAGTATCTGATTTGT
      K   S   D   F   K   K   Y   V   E   N   R   P   V   T   P   V   S   D   L   S    72
 301 CAGAGGAAGAGAATCTGCTTCCGGGAACACCTGATTTTCATACAATCCCAGCATTTTGTT
      E   E   E   N   L   L   P   G   T   P   D   F   H   T   I   P   A   F   C   L    92
 361 TGACTCCACCTTACAGTCCTTCTGACTTTGAACCCTCTCAAGTGTCAAATCTGATGGCAC
      T   P   P   Y   S   P   S   D   F   E   P   S   Q   V   S   N   L   M   A   P   112
 421 CAGCGCCATCTACTGTACACTTCAAGTCACTCTCAGATACTGCCAAACCTCACATTGCCG
      A   P   S   T   V   H   F   K   S   L   S   D   T   A   K   P   H   I   A   A   132
 481 CACCTTTCAAAGAGGAAGAAAAGAGCCCAGTATCTGCCCCCAAACTCCCCAAAGCTCAGG
      P   F   K   E   E   E   K   S   P   V   S   A   P   K   L   P   K   A   Q   A   152
 541 CAACAAGTGTGATTCGTCATACAGCTGATGCCCAGCTATGTAACCACCAGACCTGCCCAA
      T   S   V   I   R   H   T   A   D   A   Q   L   C   N   H   Q   T   C   P   M   172
 601 TGAAAGCAGCCAGCATCCTCAACTATCAGAACAATTCTTTTAGAAGAAGAACCCACCTAA
      K   A   A   S   I   L   N   Y   Q   N   N   S   F   R   R   R   T   H   L   N   192
 661 ATGTTGAGGCTGCAAGAAAGAACATACCATGTGCCGCTGTGTCACCAAACAGATCCAAAT
      V   E   A   A   R   K   N   I   P   C   A   A   V   S   P   N   R   S   K   C   212
 721 GTGAGAGAAACACAGTGGCAGATGTTGATGAGAAAGCAAGTGCTGCACTTTATGACTTTT
      E   R   N   T   V   A   D   V   D   E   K   A   S   A   A   L   Y   D   F   S   232
 781 CTGTGCCTTCCTCAGAGACGGTCATCTGCAGGTCTCAGCCAGCCCCTGTGTCCCCACAAC
      V   P   S   S   E   T   V   I   C   R   S   Q   P   A  [P   V   S   P] Q   Q   252
 841 AGAAGTCAGTGTTGGTCTCTCCACCTGCAGTATCTGCAGGGGAGTGCCACCTATGCCGG
      K   S   V   L   V   S   P   P   A   V   S   A   G   G   V  [P   P   M   P] V   272
 901 TCATCTGCCAGATGGTTCCCCTTCCTGCCAACAACCCTGTTGTGACAACAGTCGTTCCCA
      I   C   Q   M   V   P   L   P   A   N   N   P   V   V   T   T   V   V   P   S   292
 961 GCACTCCTCCCAGCCAGCCACCAGCCGTTTGCCCCCTGTTGTGTTCATGGGCACACAAG
      T   P  [P   S   Q   P] P   A   V   C   P   P   V   V   F   M   G   T   Q   V   312
1021 TCCCCAAAGGCGCTGTCATGTTTGTGGTACCCCAGCCCGTTGTGCAGAGTTCAAAGCCTC
      P   K   G   A   V   M   F   V   V   P   Q   P   V   V   Q   S   S   K   P   P   332
1081 CGGTGGTGAGCCCGAATGGCACCAGACTCTCTCCCATTGCCCCTGCTCCTGGGTTTTCCC
      V   V   S   P   N   G   T   R   L   S  [P   I   A   P] A   P   G   F   S   P   352
1141 CTTCAGCAGCAAAAGTCACTCCTCAGATTGATTCATCAAGGATAAGGAGTCACATCTGTA
      S   A   A   K   V   T   P   Q   I   D   S   S   R   I   R   S   H   I  [C   S]  372
1201 GCCACCCAGGATGTGGCAAGACATACTTTAAAAGTTCCCATCTGAAGGCCCACACAGGA
     [H   P   G   C   G   K   T   Y   F   K   S   S   H   L   K   A   H   T   R   T]  392
1261 CGCACACAGGAGAAAAGCCTTTCAGCTGTAGCTGGAAAGGTTGTGAAAGGAGGTTTGCCC
     [H]  T   G   E   K   P   F   S  [C   S   W   K   G   C   E   R   R   F   A   R]  412
1321 GTTCTGATGAACTGTCCAGACACAGGCGAACCCACACGGGTGAGAAGAAATTTGCGTGCC
      S   D   E   L   S   R   H   R   R   T   H]  T   G   E   K   K   F   A  [C   P]  432
1381 CCATGTGTGACCGGCGGTTCATGAGGAGTGACCATTTGACCAAGCATGCCCGGCGCCATC
     [M   C   D   R   R   F   M   R   S   D   H   L   T   K   H   A   R   R   H] L   452
1441 TATCAGCCAAGAAGCTACCAAACTGGCAGATGGAAGTGAGCAAGCTAAATGACATTGCTC
      S   A   K   K   L   P   N   W   Q   M   E   V   S   K   L   N   D   I   A   L   472
1501 TACCTCCAACCCCTGCTCCCACACAGTGACAGACCGGAAAGTGAAGAGTCAGAACTAACT
      P   P   T   P   A   P   T   Q   *                                                 480
1561 TTGGTCTCAGCGGGAGCCAGTGGTGATGTAAAAATGCTTCCACTGCAAGTCTGTGGCCCC
1621 ACAACGTGGGCTTAAAGCAGAAGCCCCACAGCCTGGCACGAAGGCCCCGCCTGGGTTAGG
1681 TGACTAAAAGGGCTTCGGCCACAGGCAGGTCACAGAAAGGCAGGTTTCATTTCTTATCAC
1741 ATAAGAGAGATGAGAAAGCTTTTATTCCTTTGAATATTTTTGAAGGTTTCAGATGAGGT
1801 CAACACAGGTAGCACAGATTTTGAATCTGTGTGCATATTTGTTACTTTACTTTTGCTGTT
1861 TATACTTGAGACCAACTTTTCAATGTGATTCTTCTAAAGCACTGGTTTCAAGAATATGGA
1921 AGCTGGAAGGAAATAAACATTACGGTACAGACATGGAGATGTAAAATGAGTTTGTATTAT
1981 TACAAATATTGTCATCTTTTTCTAGAGTTATCTTCTTTATTATTCCTAGTCTTTCCAGTC
2041 AACATCGTGGATGTAGTGATTAAATATATCTAGAACTATCATTTTTACACTATTGTGAAT
2101 ATTTGGAATTGAACGACTGTATATTGCTAAGAGGGCCCAAAGAATTGGAATCCTCCTTAA
2161 TTTAATTGCTTTGAAGCATAGCTACAATTTGTTTTTGCATTTTTGTTTTGAAAGTTTAAC
2221 AAATGACTGTATCTAGGCATTTCATTATGCTTTGAACTTTAGTTTGCCTGCAGTTTCTTG
2281 TGTAGATTTGAAAATTGTATACCAATGTGTTTTCTGTAGACTCTAAGATACACTGCACTT
2341 TGTTTAGAAAAAAAACTGAAGATGAAATATATATTGTAAAGAAGGGATATTAAGAATCTT
2401 AGATAACTTCTTGAAAAAGATGGCTTATGTCATCAGTAAAGTACCTTTATGTTATGAGGA
2461 TATAATGTGTGCTTTATTGAATTAGAAAATTAGTGACCATTATTCACAGGTGGACAAATG
2521 TTCGTCCTGTTAATTTATAGGAGTTTTTTGGGGATGTGGAGGTAGTTGGGTAGAAAAATT
2581 ATTAGAACATTCACTTTTGTTAACAGTATTTCTCTTTTATTCTGTTATATAGTGGATGAT
2641 ATACACAGTGGCAAAACAAAAGTACATTGCTTAAAATATATAGTGAAAAATGTCACTATA
2701 TCTTCCCATTTAACATTGTTTTTGTATATTGGGTGTAGATTTCTGCATCAAAACTTGGA
2761 CCCTTGGAAAACAAAAGTTTTAATTAAAAAAAATCCTTGTGACTTACAATTTGCACAATA
2821 TTTCTTTTGTTGTACTTTATATCTTGTTTACAATAAAGAATTCCCTTTGGCAAAAAAAAA
2881 A
```

FIG. 1

```
        371                                                                                           447
TIEF     CSHPGCGKTYFKSSHLKAFTRTHTGEKPFSCSWKGCERRFARSDELSRHRRTHTGEKKFACPMCDRRFMRSDELTKH
SPR-2    CHIPGCGKVYGKTSHLRAHLRWHSGERPFVCNWMYCGKRFTRSDELQRHRRTHTGEKKFVCPECSKRFMRSDELAKH
Sp3      CHIPGCGKVYGKTSHLRAHLRWHSGERPFVCNWMYCGKRFTRSDELQRHRRTHTGEKKFVCPECSKRFMRSDELAKH
SPR-1    CHIEGCGKVYGKTSHLRAHLRWHTGERPFICNWMFCGKRFTRSDELQRHRRTHTGEKRFECPECSKRFMRSDELSKH
Sp1      CHIQGCGKVYGKTSHLRAHLRWHTGERPFMCTWSYCGKRFTRSDELQRHRKRTHTGEKKFACPECPKRFMRSDELSKH
BTEB     CDYPGCTKVYTKSSHLKAHLRTHTGEKPYKCTWEGCDWRFARSDELTRHYRKHTGAKPFQCGVCNRSFSRSDELALH
MUS Krp  CGHEGCGKSYSKSSHLKAHLRTHTGEKPYACSWDGCDWRFARSDELTRHYRKHTGHRPFCCGLCPRAFSRSDELALH
Sp2      CHIPDCGKTFRKTSLLRAHVRLHTGERPFVCNWFFCGKRFTRSDELQRHARTHTGDKRFECAQCQKRFMRSDELTKH
WT-1     CAYPGCNKRYFKLSELQMHSRKHTGEKPYQCDFKDCERRFSRSDQLKRHQRRHTGVKPFQCKTCQRKFSRSDELKTH
```

FIG. 2

TGF-β INDUCIBLE EARLY FACTOR-1 (TIEF-1) AND A METHOD TO DETECT BREAST CANCER

BACKGROUND OF THE INVENTION

Breast and endometrial carcinomas remain major oncological problems. Both types of cancers are considered to be responsive to endocrine therapy. This is particularly true in the case of breast cancer, whether one considers ablative or additive therapy. However, tumor responses to steroid therapy vary significantly among these tumors. In general, for breast carcinoma, only half of the tumors of estrogen receptor (ER)-positive breast cancer patients, assessed by the dextran-coated charcoal assay (DCC assay) (see U.S. Pat. No. 5,030,417; Thibodeau et al., *Clin. Chem.*, 27, 687 (1981)), respond to estrogen (E) therapy. Moreover, 80% of all breast cancer metastases to bone are ER positive. Although the ER and PR (progesterone receptor; Thibodeau et al., *Clin. Chem.*, 27, 687 (1981)) assays currently in use clinically have improved a physician's ability to predict a response to hormonal therapy, the DCC assay has a relatively high false-positive rate (Ingle, *Cancer*, 53, 766 (1984)). Furthermore, the lack of response to estrogen therapy by many ER-positive patients indicates the need for an assay with estrogen-related markers that have a substantially higher predictive index than the DCC assay.

The breast cancer genes BRCA-1 and BRCA-2 appear to be involved in the inherited susceptibility of breast cancer. Both BRCA-1 and BRCA-2 genes encode polypeptides having homology domains and properties of a granin family of proteins (Schuard et al., *Endocrine Reviews*, 14, 659 (1993); Steeg, *Nat. Gene.*, 12, 223 (1996); Jensen et al., *Nat. Genet.*, 12, 303 (1996); Holt et al., *Nat. Genet.*, 12, 298 (1996); Wooster et al., *Science*, 265, 2088 (1995)). Overexpresssion of the BRCA genes inhibits, and underexpression encourages, tumor growth. The p53 gene, a tumor suppressor gene, and the BRCA-1 gene, which exhibits properties of a tumor suppressor gene, are regulated by estrogen in breast cancer cells.

Transforming growth factor-beta (TGB-β) is produced by breast cancer cells and can inhibit breast cancer cell growth (Valverius et al., *Cancer Res.*, 49, 6269 (1989); Knabbe et al., *Cell*, 48, 417 (1987)). The production and activation of TGF-β is regulated by estrogen, parathyroid hormone, glucocorticoids, and other bone regulatory agents including TGF-β itself (Oursler et al., *Endocrinology*, 129, 3313 (1991); Oursler et al., *Endocrinology*, 133, 2187 (1993); Subramaniam et al., *J. Cell. Biochem.*, 57, 52 (1995)). More recently, TGF-β has been implicated in the antiestrogen-induced apoptosis of breast cancer cells (Chen et al., *J. Cell, Biochem.*, 61, 9 (1996)).

Thus, a continuing and urgent need exists for an accurate determinant marker effective to ascertain the most efficacious therapy of breast cancers. In particular, there is a need to identify and isolate estrogen and TGF-β regulated genes, the expression of which are predictive of a breast or endometrial cancer patient's response to steroid therapy or the metastatic potential of these cancers. Moreover, there is also a need to identify and isolate genes that may be tumor suppressor genes for both breast and endometrial carcinomas.

SUMMARY OF THE INVENTION

The present invention provides an isolated and purified DNA molecule comprising a DNA sequence encoding TGF-β inducible early factor-1 (TIEF-1), or a biologically active subunit or variant thereof. A preferred embodiment of the invention is a DNA sequence, eg., SEQ ID NO:1, that encodes a polypeptide having an amino acid sequence comprising SEQ ID NO:2. Also provided is an isolated and purified DNA molecule which is complementary to the DNA molecules described hereinabove.

The DNA molecules of the invention are double-stranded or single-stranded, preferably, they are cDNA. A preferred embodiment of the invention includes a DNA molecule that has at least about 80%, preferably at least about 90%, and more preferably at least about 95%, identity to the DNA sequence comprising SEQ ID NO:1. Thus, a preferred embodiment of the invention includes a DNA molecule which has at least about 80%, preferably at least about 90%, and more preferably at least about 95%, identity to SEQ ID NO:1.

As described hereinbelow, TIEF-1 expression is rapidly induced by TGF-β, and estrogen (E), administration. The induction of TIEF-1 expression by estrogen is dependent on the presence of the estrogen receptor (ER) in cells. The TIEF-1 gene encodes three zinc finger motifs, domains of which are known to bind nucleic acid. Moreover, the C-terminal region of TIEF-1 contains a proline-rich region, which may have a transcriptional activating function.

As used herein, "TIEF-1" is preferably a polypeptide comprising SEQ ID NO:2, as well as variants of SEQ ID NO:2 which have at least about 80%, preferably at least about 90%, and more preferably at least about 95%, identity or homology to SEQ ID NO:2, or a biologically active subunit thereof. Biologically active subunits of TIEF-1, e.g., peptides comprising SEQ ID NO:4 or SEQ ID NO:5, variant TIEF-1 polypeptides and biologically active subunits thereof, falling within the scope of the invention have at least about 10%, preferably at least about 50%, and more preferably at least about 90%, the activity of the polypeptide comprising SEQ ID NO:2. The activity of a polypeptide or peptide of the invention can be measured by methods well known to the art including, but not limited to, the ability of the polypeptide or peptide to elicit a sequence-specific immunologic response when the peptide is administered to a mammal, e.g., goat, rabbit, sheep or mice (see Example 3).

An isolated and purified DNA molecule of the invention, such as a probe or a primer, of at least seven nucleotide bases which hybridizes to the DNA molecules, or RNA molecules derived from these DNA molecules, is useful to detect, quantify and amplify complementary DNA stands in eukaryotic tissue samples comprising TIEF-1 sequences or sequences related to TIEF-1. The cDNAs of the present invention are useful for detecting the expression of TIEF-1, for detecting related DNA molecules and for amplifying nucleic acid sequences, wherein said sequences fall within the scope of the present invention.

The invention also provides an expression cassette comprising a preselected DNA sequence encoding TIEF-1, or a biologically active subunit or variant thereof, which is operably linked to a promoter functional in a host cell. Such expression cassettes can be incorporated into expression vectors which can then be employed to transform prokaryotic or eukaryotic host cells, so as to result in expression of TIEF-1 polypeptide. The present vectors can also contain a functional DNA sequence which is a selectable marker gene and/or reporter gene, as described below. Therefore, therapeutic compositions containing TIEF-1 polypeptide, subunits of TIEF-1, or variants thereof, are also within the scope of the invention.

Also provided is an expression cassette comprising: a preselected DNA segment that is complementary to a DNA sequence encoding TIEF-1, e.g., SEQ ID NO:1, which is operably linked to a promoter functional in a host cell. Thus, the present invention provides an expression cassette which expresses an "anti-sense" mRNA transcript of a DNA sequence of the invention. When this transcript is introduced into a host cell, it can alter TIEF-1 expression, as well as cell growth and/or differentiation of the host cell.

Further provided is an isolated and purified TIEF-1 polypeptide, or a biologically active subunit or variant thereof. Also provided are isolated, purified peptides of TIEF-1, or biologically active variants thereof e.g., a peptide comprising SEQ ID NO:4 or SEQ ID NO:5. A preferred TIEF-1 polypeptide comprises an amino acid sequence corresponding to SEQ ID NO:2. TIEF-1 polypeptide or a TIEF-1 peptide can be employed to prepare antibodies specific for TIEF-1.

Thus, the invention also provides a purified antibody, or a preparation of polyclonal or monoclonal antibodies, that specifically reacts with TIEF-1 protein or polypeptide. A preferred antibody of the invention is a polyclonal antibody that specifically binds to TIEF-1. The antibodies of the invention are useful to detect TIEF-1 levels in patient samples (see Example 3).

The invention further provides a method of expressing a DNA sequence encoding TIEF-1, or a biologically active subunit or variant thereof he method comprises introducing the DNA sequence which is operably linked to a promoter functional in a host cell into the host cell. The DNA sequence is expressed in the host cell so as to yield TIEF-1. Preferably, the TIEF-1 is then recovered from the host cell.

Yet another embodiment of the invention is a method for detecting or determining TIEF-1 in a sample of a human physiological material which may contain TIEF-1. The method comprises contacting an amount of purified antibodies which specifically react with TIEF-1 with the sample to be tested. The antibodies are contacted with the sample for a sufficient time to allow the formation of binary complexes between at least a portion of the antibodies and a portion of TIEF-1. The presence or amount of TIEF-1 complexed with said antibodies is then determined or detected.

The invention further provides a diagnostic method for detecting breast cancer in a female human at risk of, or afflicted with, the disease. The method comprises contacting an amount of purified antibodies which specifically react with TIEF-1 with a sample obtained from said female to be tested. The antibodies are contacted with the sample for a sufficient time to allow the formation of binary complexes between at least a portion of the antibodies and a portion of TIEF-1 present in said sample. The presence or amount of TIEF-1 complexed with said antibodies is then determined or detected. The absence of the complexes is indicative of a female at risk of, or afflicted with, breast cancer. The results presented hereinbelow show reduced levels of TIEF-1 are present in in situ breast carcinoma, and undetectable levels of TIEF-1 are present in invasive breast cancer. Thus, the absence of TIEF-1, or low levels of TIEF-1, may be indicative of aggressive breast cancer.

Further provided is a method for monitoring the progression of breast cancer in a patient. The method comprises contacting an amount of purified antibodies which specifically react with TIEF-1 with a sample to be tested, for a sufficient time to allow the formation of binary complexes between at least a portion of the antibodies and a portion of TIEF-1. The presence or amount of the complexes is detected or determined. At a later point in time, the presence or amount of TIEF-1 in a second sample from the same patient is detected or determined and the results from the two samples are compared. The first sample can be tested prior to the patient undergoing anti-cancer therapy, and the subsequent samples can be tested after therapy and/or during remission.

Yet another embodiment of the invention is a diagnostic kit for detecting or determining TIEF-1 in a mammalian physiological sample. The kit comprises packaging, containing, separately packaged: (a) a solid phase capable of having attached thereto, an amount of antibodies that bind TIEF-1; and (b) a known amount of antibodies which specifically bind TIEF-1.

A further embodiment of the invention is a diagnostic kit for detecting or determining TIEF-1 in a mammalian physiological sample. The kit comprises packaging, containing, separately packaged: (a) a known amount of a first antibody which specifically binds to TIEF-1; and (b) a known amount of a second antibody which specifically binds to TIEF-1.

The invention also provides methods to detect genetic rearrangements in the TIEF-1 gene. The method comprise contacting a first amount of a labeled probe comprising a preselected DNA encoding TIEF-1 with a sample which comprises mammalian cells suspected of containing an amplified TIEF-1 gene, for a sufficient time to form binary complexes between at least a portion of said amount of said probe and the cells in the sample. The amount of said binary complexes is determine or detected relative to the amount of binary complexes formed between at least a portion of a second amount of said probe and a sample comprising mammalian cells which do not contain an amplified TIEF-1 gene. A greater amount of binary complexes formed from the sample which comprises mammalian cells suspected of containing an amplified TIEF-1 gene is indicative of amplification of the TIEF-1 gene. Alternatively, the amount of binary complexes formed from the sample which comprises mammalian cells suspected of containing an amplified TIEF-1 gene is compared to the amount of binary complexes formed between at least a portion of a second labeled probe which does not comprise DNA encoding TIEF-1 and which does not comprise a gene which is amplified and the sample, or a second amount of said sample.

Also provided is a method to detect genetic rearrangements of the TIEF-1 gene in a mammalian physiological sample suspected of containing a genetically rearranged TIEF-1 gene. The method comprises contacting an amount of a labeled probe comprising a preselected DNA encoding TIEF-1 with genomic DNA isolated from the sample for a sufficient time to allow the formation of binary complexes between at least a portion of said probe and the genomic DNA in the sample. The absence or presence of said binary complexes is compared to the absence or presence of control binary complexes formed between at least a portion of said probe and genomic DNA isolated from a sample comprising mammalian cells which do not contain a genetically rearranged TIEF-1 gene. The presence of complexes formed between at least a portion of said probe and the genomic DNA in the sample suspected of containing a genetically rearranged TIEF-1 gene that are different than the control complexes formed is indicative of a genetically rearranged TIEF-1 gene.

Further provided is a method to determine genetic rearrangements of the TIEF-1 gene in a mammalian physiological sample suspected of containing a genetically rearranged TIEF-1 gene. The method comprises subjecting DNA isolated from the sample to a polymerase chain reaction using a plurality of primers under reaction conditions sufficient to amplify at least a portion of the TIEF-1 gene to produce an amplification product. It is then determined whether the amplification product is different than an amplification product obtained by subjecting DNA isolated from a sample which does not comprise genetic rearrangements of the TIEF-1 gene to a polymerase chain reaction using the plurality of said primers under said reaction conditions sufficient to amplify at least a portion of said TIEF-1 gene.

BRIEF DESCRIPTION OF THE FIGURES

FIG. 1. cDNA sequence of TIEF-1. Nucleotide sequence (SEQ ID NO:1) and deduced amino acid sequence (SEQ ID NO:2) of TIEF-1 cDNA. The first "M" in the amino acid sequence denotes the translational start site. The stop codon is shown with an asterisk. The shaded amino acids show the three zinc finger motifs. The proline-rich region src homology-3 (SH3) binding domains are shown in boxes. The underlined nucleotides indicate the polyadenylation signal sequence and AUUUA motifs. The numbers on the left denote the nucleotides and the numbers on the right refer to the amino acid residues.

FIG. 2. A diagram showing the homology of the zinc finger region of the TIEF-1 protein to other members of this family. The conserved cysteine and histidine residues in the zinc finger motif are shown in bold letters. The highly conserved amino acids in TIEF-1 and other members of this gene family are underlined. The numbers denote the amino acid positions of TIEF-1. TIEF-1=TGF-β inducible early factor-1, SPR-2=human GT box binding protein (SEQ ID NO:6), Sp3=human Sp3 protein (SEQ ID NO:7), SPR-1= human GT box binding protein (SEQ ID NO:8), Sp1=human transcription factor Sp1 (SEQ ID NO:9), BTEB=human GC box binding protein (SEQ ID NO:10), MUSKrp=mouse erythroid Krueppel-like transcription factor (SEQ ID NO:11), Sp2=human Sp2 protein (SEQ ID NO:12), and WT-1=human Wilm's tumor zinc finger protein (SEQ ID NO:13).

DETAILED DESCRIPTION OF THE INVENTION

Figure 3:
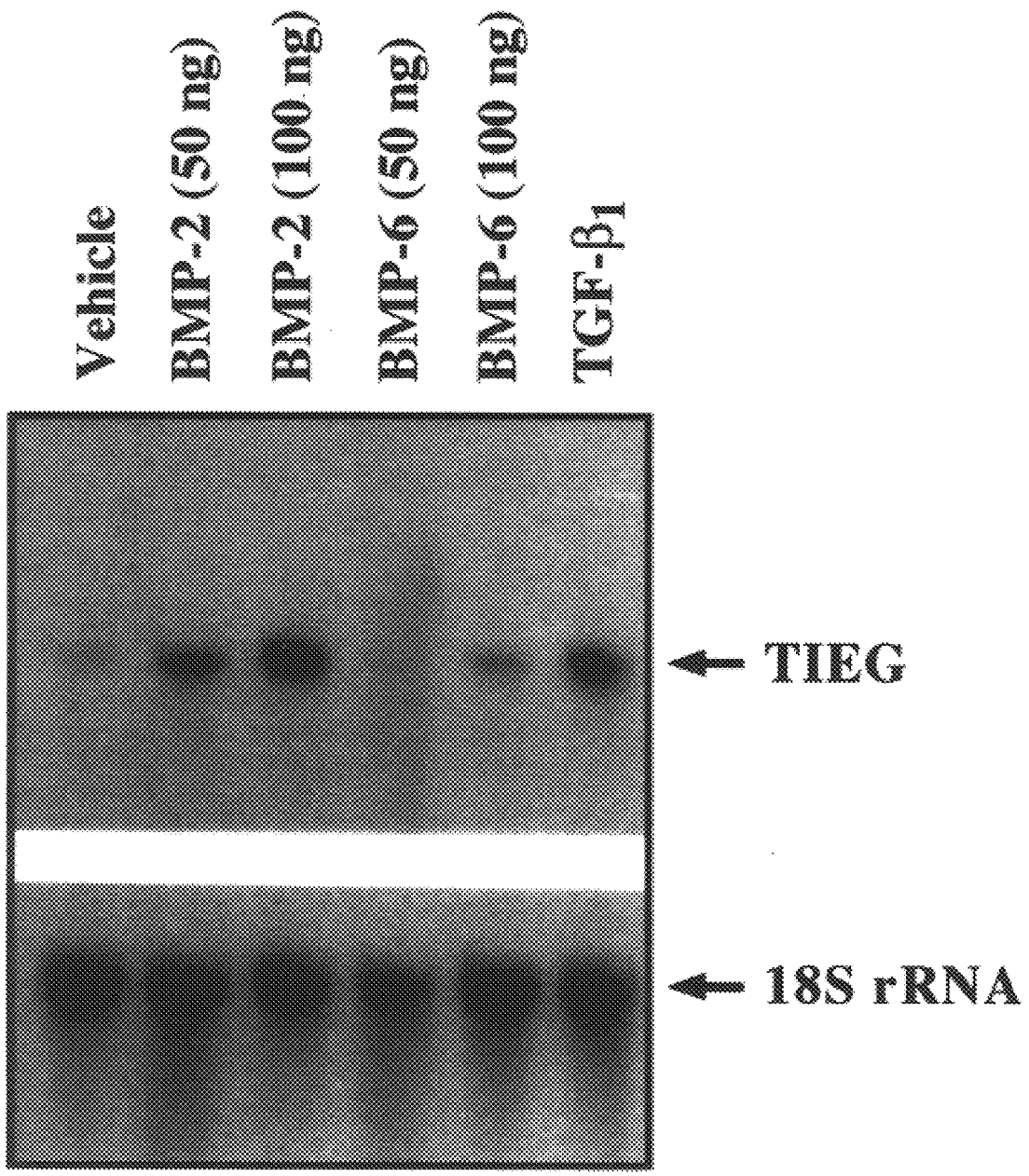
FIG. 3. Northern blot analysis of mRNA extracted from human bone cells treated with vehicle, BMP-2, BMP-6, or TGF-β for 90 minutes. The mRNA was probed with a TIEF-1 or 18S radiolabeled probe.

In order to more fully understand the mechanism by which a gene which is rapidly induced by TGF-β, i.e., TIEF-1, influences cell growth in normal and neoplastic tissue, cDNAs which encode TIEF-1 were isolated. Besides identifying the gene encodig TIEF-1 which may play a role in, or be associated with, cell growth and differentiation in normal cells, e.g., breast or endometrial cells, the identification and isolation of DNAs encoding a TIEF-1 may be useful to define the molecular basis for some neoplastic processes, to provide a clinically useful diagnostic test, or in molecular-based therapeutics.

Once a correlation has been identified between the levels of TIEF-1 and a particular disease, e.g., breast, colon, endometrial, prostate or blood (leukemia) cancers, patient samples, e.g., tissue biopsies, can then be analyzed with antibodies specific for TIEF-1. The presence or amount of TIEF-1 in the patient is compared to the presence or amount of TIEF-1 in disease-free patients. Moreover, the levels of TIEF-1 in a patient can be used as an indicator of the histological status, estrogen receptor status, tumor grade, metastatic disease, responsiveness to therapy or overall survival.

Furthermore, the cloning of transcripts encoding TIEF-1 will elucidate the molecular mechanism giving rise to the presence or absence of TIEF-1 in patients with disease. Molecular genetic-based therapies directed to controlling the expression of TIEF-1 can then be employed to correct, inhibit or supplement the expression of TIEF-1 in patients with the disease. For example, an expression vector containing DNA encoding TIEF-1 can be introduced into tumor cells to inhibit or reduce tumor growth or proliferation.

The cDNAs encoding TIEF-1 can also be employed in expression cassettes to synthesize TIEF-1, a biologically active variant thereof, or a biologically active subunit thereof, in vitro. In vitro prepared TIEF-1 can be employed to obtain antibodies specific for TIEF-1. In vitro synthesized TIEF-1 polypeptide may also be employed in a pharmaceutical formulation which, when administered to a human, can suppress or block tumor cell growth.

Sources of Nucleic Acids Encoding TIEF-1

Sources of nucleotide sequences from which the present DNA molecules encoding TIEF-1 include total or polyA$^+$ RNA from any eukaryotic, preferably mammalian, cellular source, preferably total or polyA$^+$ RNA from mammalian osteoblastic, osteoclastic, or muscle skeletal cells, as well as RNA isolated from tissue samples of bone, breast, colon, heart, pancreas, endometrium, placenta and the like, from which the cDNA encoding TIEF-1 can be derived by methods known in the art. Other sources of the DNA molecules of the invention include cDNA or genomic libraries derived from any eukamyotic cellular source.

Isolation of a Gene Encoding TIEF-1

A nucleic acid molecule encoding TIEF-1 can be identified and isolated using standard methods, as described by Sambrook et al., *Molecular Cloning: A Laboratory Manual*, Cold Spring Harbor, N.Y. (1989). For example, differential display PCR can be employed to isolate and clone genes induced by TGF-β.

Polymerase chain reaction or "PCR" is a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers comprising at least 7–8 nucleotides. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., *Cold Spring Harbor Symp. Quant. Biol.*, 51, 263 (1987); Erlich, ed., *PCR Technology*, (Stockton Press, NY, 1989). Thus, PCR-based cloning approaches generally rely upon conserved sequences deduced from alignments of related gene or polypeptide sequences.

Total RNA is isolated from cells treated with either vehicle or TGF-$\beta_1$. RNA can be isolated by methods known to the art, e.g., using TRIZOL™ reagent (GIBCO-BRL/Life Technologies, Gaithersburg, Md.). Total RNA is then treated with RNAse-free DNAse to remove any DNA contamination. DNA-free RNA from control and TGF-$\beta_1$-treated cells is used as a template for first strand cDNA synthesis in the presence of degenerate anchored oligo-dT primers. The synthesized first strand cDNA is used as a template in a PCR reaction. After the PCR is completed, the sample is run on a gel, and the gel is analyzed for differentially expressed genes. Differentially expressed genes are gel-purified and cloned directly into a suitable vector, such as a known plasmid vector. The resultant plasmids are subjected to restriction endonuclease and dideoxy sequencing of double-stranded plasmid DNAs.

Another approach to identify and isolate cDNAs which encode TIEF-1 is to employ reverse-transcriptase PCR (RT-PCR). Oligo-dT can be employed as a primer in a reverse transcriptase reaction to prepare first-strand cDNAs from isolated RNA which contains RNA sequences of interest, e.g., total RNA isolated from human osteoblast cells. Resultant first-strand cDNAs are then amplified in PCR reactions.

Primers are made to correspond to highly conserved regions of polypeptides or nucleotide sequences which were identified and compared to generate the primers, e.g., by a sequence comparison of known TIEF-1 genes. One primer is prepared which is predicted to anneal to the antisense strand, and another primer prepared which is predicted to anneal to the sense strand, of a DNA molecule which encodes TIEF-1.

The products of each PCR reaction are separated via an agarose gel and all consistently amplified products are gel-purified and cloned directly into a suitable vector, such as a known plasmid vector. The resultant plasmids are subjected to restriction endonuclease and dideoxy sequencing of double-stranded plasmid DNAs.

Figure 4:
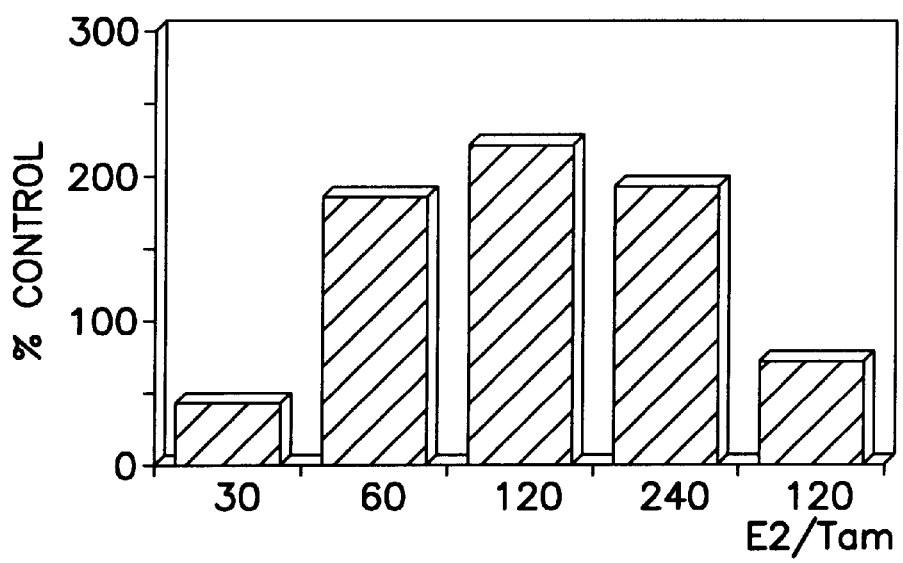
FIG. 4. E2 (17-β-estradiol) treatment upregulates TIEF-1 mRNA levels in an ER(+) breast cancer cell line, MCF7. Subconfluent MCF7 cells (70%) were serum-starved in DMEM/F12 containing 0.25% BSA for 48 hours prior to E2 (Sigma Chemical Co., St. Louis, Mo.) treatment. Cells were treated with 10 nM E2 or the equivalent volume of ethanol (evaporated to dryness). Total RNA was obtained at the times indicated post-treatment. Tamoxifen (Tam, 10 nM) was dried and resuspended with 10 nM E2. The vehicle control and Tam/E2 treated cells were harvested at 120 minutes post-treatment. Densitometric analysis of the autoradiographs was performed and the mRNA levels for TIEF-1 were normalized to the levels of 18S rRNA.

As used herein, the terms "isolated and/or purified" refer to in vitro isolation of a DNA or polypeptide molecule from its natural cellular environment, and from association with other components of the cell, such as nucleic acid or polypeptide, so that it can be sequenced, replicated, and/or expressed. For example, "isolated TIEF-1 nucleic acid" is RNA or DNA containing greater than 7, preferably 15, and more preferably 20 or more, sequential nucleotide bases that encode a biologically active TIEF-1 polypeptide or a fragment thereof, or a biologically active variant TIEF-1 polypeptide or a fragment thereof, that is complementary to the non coding strand, or complementary to the coding strand, of the native TIEF-1 polypeptide RNA, or hybridizes to RNA or DNA encoding TIEF-1 and remains stably bound under stringent conditions, as defined by methods well known in the art, e.g., in Sambrook et al., supra. Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell. An example of isolated TIEF-1 nucleic acid is RNA or DNA that encodes a biologically active TIEF-1 polypeptide sharing at least about 80%, preferably at least about 90%, and more preferably at least about 95%, amino acid sequence identity with the TIEF-1 polypeptide of FIG. 4.

As used herein, the term "recombinant nucleic acid" or "preselected nucleic acid," e.g., "recombinant DNA sequence or segment" or "preselected DNA sequence or segment" refers to a nucleic acid, i.e., to DNA that has been derived or isolated from any appropriate tissue source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., *Nucleic Acids Res.*, 9, 6103 (1981), and Goeddel et al., *Nucleic Acids Res.*, 8, 4057 (1980). Therefore, "preselected DNA" includes completely synthetic DNA sequences, semi-synthetic DNA sequences, DNA sequences isolated from biological sources, and DNA sequences derived from RNA, as well as mixtures thereof.

As used herein, the term "derived" with respect to a RNA molecule means that the RNA molecule has complementary sequence identity to a particular DNA molecule.

Variants of the DNA Molecules of the Invention

Nucleic acid molecules encoding amino acid sequence variants of TIEF-1 are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of TIEF-1 polypeptide.

Oligonucleotide-mediated mutagenesis is a preferred method for preparing amino acid substitution varants of TIEF-1. This technique is well known in the art as described by Adelman et al., *DNA*, 2, 183 (1983). Briefly, TIEF-1 DNA is altered by hybridizing an oligonucleotide encoding the desired mutation to a DNA template, where the template is the single-stranded form of a plasmid or bacteriophage containing the unaltered or native DNA sequence of TIEF-1. After hybridization, a DNA polymerase is used to synthesize an entire second complementary strand of the template that will thus incorporate the oligonucleotide primer, and will code for the selected alteration in the TIEF-1 DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. U.S.A.*, 75, 5765 (1978).

The DNA template can be generated by those vectors that are either derived from bacteriophage M13 vectors (the commercially available M13mp 18 and M13 mp 19 vectors are suitable), or those vectors that contain a single-stranded phage origin of replication as described by Viera et al., *Meth. Enzymol.*, 153, 3 (1987). Thus, the DNA that is to be mutated may be inserted into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, N.Y. 1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of TIEF-1, and the other strand (the original template) encodes the native, unaltered sequence of the TIEF-1. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for polypeptide production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(aS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101.

A preferred embodiment of the invention is an isolated and purified DNA molecule comprising a preselected DNA sequence encoding a TIEF-1 polypeptide comprising SEQ ID NO:2, wherein the DNA segment comprises SEQ ID NO:1, or variants of SEQ ID NO:1, having nucleotide substitutions which are "silent." That is, when nucleotide substitutions are present in a codon, the same amino acid is encoded by the codon with the nucleotide substitution as is encoded by the codon without the substitution. For example, leucine is encoded by the codon CTT, CTC, CTA and CTG. A variant of SEQ ID NO:1 at the second codon in the polypeptide (CTC in SEQ ID NO:1) includes the substitution of CTT, CTG or CTA for CTC. Other "silent" nucleotide substitutions in SEQ ID NO:1 which can encode a polypeptide having SEQ ID NO:2 can be ascertained by reference to page D1 in Appendix D in Sambrook et al., *Molecular Cloning: A Laboratory Manual* (1989). Nucleotide substitutions can be introduced into DNA segments by methods well known to the art. See, for example, Sambrook et al., supra.

Chimeric Expression Cassettes

As used herein, "chimeric" means that a vector comprises DNA from at least two different species, or comprises DNA from the same species, which is linked or associated in a manner which does not occur in the "native" or wild type of the species.

The recombinant or preselected DNA sequence or segment, used to prepare expression cassettes for transformation, may be circular or linear, double-stranded or single-stranded. Generally, the preselected DNA sequence or segment is in the form of chimeric DNA, such as plasmid DNA, that can also contain coding regions flanked by control sequences which promote the expression of the preselected DNA present in the resultant cell fine. Aside from preselected DNA sequences that serve as transcription units for TIEF-1 or portions thereof, a portion of the preselected DNA may be untranscribed, serving a regulatory or a structural function. For example, the preselected DNA may itself comprise a promoter that is active in mammalian cells, or may utilize a promoter already present in the genome that is the transformation target. Such promoters include the CMV promoter, as well as the SV40 late promoter and retoviral LTRs (long terminal repeat elements), although many other promoter elements well known to the art may be employed in the practice of the invention. A preferred promoter useful in the practice of the invention is the murine sarcoma virus LTR.

Other elements functional in the host cells, such as introns, enhancers, polyadenylation sequences and the like, may also be a part of the preselected DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a polypeptide if it is expressed as a prepolypeptide that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The preselected DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA and the like. See also, the genes listed on Table 1 of Lundquist et al. (U.S. Pat. No. 5,848, 956).

Reporter genes are used for identifying potentially transformed cells and for evaluating the functionality of regulatory sequences. Reporter genes which encode for easily assayable polypeptides are well known in the art. In general, a reporter gene is a gene which is not present in or expressed by the recipient organism or tissue and which encodes a polypeptide whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Mnanual,* Cold Spring Harbor Laboratory Press (2d ed, 1989), provides suitable methods of construction. A preferred expression cassette useful to express TIEF-1 includes pMEXneo. pMEXneo comprises the murine sarcoma virus LTR and the neo gene as a selectable marker.

Transformation into Host Cells

The recombinant DNA can be readily introduced into host cells, e.g., mammalian, bacterial, yeast or insect cells by transfection with an expression vector comprising DNA encoding TIEF-1 by any procedure useful for the introduction into a particular cell, e.g., calcium phosphate precipitation, lipofection, electroporation, and the like, to yield a transformed cell having the cDNA stably integrated into its genome, so that the DNA molecules, sequences, or segments, of the present invention are expressed by the host cell. That is, the present invention also provides a transformed host cell having a genome augmented by a recombinant (non-native) DNA sequence, preferably by a chromosomally integrated recombinant (genetically engineered) DNA sequence that includes a gene encoding a TIEF-1.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including plant, insect, yeast, fungal or bacterial sources. Generally, the preselected DNA sequence is related to a DNA sequence which is resident in the genome of the host cell but is not expressed, or not highly express, or, alternatively, overexpressed.

"Transfected" or "transformed" is used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered DNA," "non-native DNA," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence. Preferably, the transfected DNA is a chromosomally integrated recombinant DNA sequence, which comprises a gene encoding TIEF-1, which host cell may or may not express significant levels of autologous or "native" TIEF-1.

TIEF-1 Polypeptides

The present invention provides an isolated, purified TIEF-1 polypeptide, which is preferably prepared by recombinant DNA methodologies. The general methods for isolating and purifying a recombinantly expressed protein from a host cell are well known to those in the art. Examples of the isolation and purification of such proteins are given in Sambrook et al., cited supra. Moreover, since the present invention provides the complete amino acid sequence of TIEF-1 (FIG. 1), it or bioactive variants thereof can also be synthesized by the solid phase peptide synthetic method. This established and widely used method, including the experimental procedures, is described in the following references: Stewart et al., *Solid Phase Peptide Synthesis,* W. H. Freeman Co., San Francisco (1969); Merrifield, *J. Am. Chem, Soc.,* 85, 2149 (1963); Meienhofer in "Hormonal Proteins and Peptides," ed.; C. H. Li, Vol. 2 (Academic Press, 1973), pp. 48–267; and Bavaay and Merrifield, "The Peptides," eds. E. Gross and F. Meienhofer, Vol. 2 (Academic Press, 1980) pp. 3–285.

When TIEF-1 polypeptide is expressed in a recombinant cell it is necessary to purify TIEF-1 polypeptide from recombinant cell proteins or polypeptides to obtain preparations that are substantially homogenous as to TIEF-1 polypeptide. For example, the culture medium or lysate can be centrifuged to remove particulate cell debris. The membrane and soluble protein fractions are then separated. The TIEF-1 polypeptide may then be purified from the soluble protein fraction. TIEF-1 polypeptide can then be purified from contamimant soluble or membrane proteins and polypeptides by fractionation on immunoaffinity or ion-exchange columns; ethanol precipitation; reverse phase HPLC; chromatography on silica or on an anion-change resin such as DEAE; chromatofocusing; SDS-PAGE; ammonium sulfate precipitation; gel filtration using, for example, Sephadex G-75; or ligand affinity chromatography, and the like.

TIEF-1 polypeptide, a variant TIEF-1 polypeptide, or a biologically active subunit thereof can also be prepared by in vitro transcription and translation reactions. A TIEF-1 expression cassette can be employed to generate TIEF-1 transcripts which are subsequently translated in vitro so as to result in a preparation of substantially homogenous TIEF-1, variant TIEF-1, or a biologically active subunit thereof. The construction of vectors for use in vitro transcription/translation reactions, as well as the methodologies for such reactions, are well known to the art.

Once isolated from the resulting transgenic host cells or from in vitro transcription/translation reactions, derivatives and chemically derived variants of the TIEF-1 polypeptide can be readily prepared. For example, amides of the TIEF-1 polypeptides of the present invention may also be prepared by techniques well known in the art for converting a carboxylic acid group or precursor, to an amide. A preferred method for amide formation at the C-terminal carboxyl group is to cleave the polypeptide from a solid support with an appropriate amine, or to cleave in the presence of an alcohol, yielding an ester, followed by aminolysis with the desired amine.

Salts of carboxyl groups of the TIEF-1 polypeptide may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the present polypeptides may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylatng reagents such as acyl halides, anhydrides, acyl imidazoles, and the like. Both N- and O-acylation may be carried out together, if desired. In addition, the internal TIEF-1 amino acid sequence of FIG. 1 can be modified by substituting one or two conservative amino acid substitutions for the positions specified, including substitutions which utilize the D rather than L form.

The invention is also directed to variant or modified forms of the TIEF-1 polypeptide. One or more of the residues of this polypeptide can be altered, so long as the variant polypeptide has at least about 10%, preferably at least about 50%, and more preferably at least about 90%, of the biological activity of the polypeptide having SEQ ID NO:2. Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids.

Acid addition salts of the polypeptides may be prepared by contacting the polypeptide with one or more equivalents of the desired inorganic or organic acid, such as, for example, hydrochloric acid. Esters of caxboxyl groups of the polypeptides may also be prepared by any of the usual methods known in the art.

TIEF-1 Variant Polypetides

It is envisioned that variant TIEF-1 polypeptides have at least one amino acid substitution relative to SEQ ID NO:2. In particular, amino acids are substituted in a relatively conservative manner. Such conservative substitutions are shown in Table 1 under the heading of exemplary substitutions. More preferred substitutions are under the heading of preferred substitutions. After the substitutions are introduced, the products are screened for biological activity.

TABLE 1

| Original Residue | Exemplary Substitutions | Preferred Substitutions |
|---|---|---|
| Ala (A) | val; leu; ile | val |
| Arg (R) | lys; gln; asn | tys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Amino acid substitutions falling within the scope of the invention, are, in general, accomplished by selecting substitutions that do not differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic; trp, tyr, phe.

The invention also envisions TIEF-1 variants with non-conservative substitutions. Non-conservative substitutions entail exchanging a member of one of the classes described above for another. Amino acid substitutions are introduced into the DNA molecules of the invention by methods well known to the art. For example, see the description hereinabove for the introduction of silent mutations into the DNA molecules of the invention.

Antibodies to TIEF-1

Once isolated, TIEF-1 polypeptide and its antigenically active variants, derivatives and fragments thereof can be used in assays for TIEF-1 in samples derived from biological materials suspected of containing TIEF-1, e.g., by employing antibodies to TIEF-1.

Both polyclonal and monoclonal antibodies to TIEF-1 can be prepared by methods well known to the art. For example, peptides of TIEF-1 can be employed as immunogens to prepare polyclonal antibodies to TIEF-1. Alternatively to the conventional techniques for preparing polyclonal antibodies or antisera in laboratory and farm animals, monoclonal antibodies against TIEF-1 polypeptide can be prepared using known hybridoma cell culture techniques. In general, this method involves prepared an antibody-producing fused cell line, e.g., of primary spleen cells fused with a compatible continuous line of myeloma cells, and growing the fused cells either in mass culture or in an animal species from which the myeloma cell line used was derived or is compatible. Such antibodies offer many advantages in comparison to those produced by inoculation of animals, as they are highly specific and sensitive and relatively "pure" immunochemically. Immunologically active fragments of the present antibodies are also within the scope of the present invention, e.g., the f(ab) fragment, as are partially humanized monoclonal antibodies.

Chimeric antibodies comprise the fusion of the variable domains from one immunoglobulin to the constant domains from another immunoglobulin. Usually, the variable domains are derived from an immunoglobulin gene from a different species, perhaps a human. This technology is well known to the art. See, for example, European Patent Applications, EP-A-0 125,023 (Cabilly/Genetech) and EP-A-0 120,694 and U.S. Pat. No. 4,816,567, the disclosures of which are incorporated by reference herein, which disclose the preparation of variations of immunoglobulin-type molecules using recombinant DNA technology.

Another approach to prepare chimeric or modified antibodies is to attach the variable region of a monoclonal antibody to another non-immunoglobulin molecule, to produce a derivative chimeric molecule (see WO 86/01533, Neuberger and Rabbits/Celltech, herein incorporated by reference). A further approach is to prepare a chimeric immunoglobulin having different specficities in its different variable regions (see EP 68763A). Yet another approach is to introduce a mutation in the DNA encoding the monoclonal antibody, so as to alter certain of its characteristics without changing its essential specificity. This can be accomplished by site-directed mutagenesis or other techniques known in the art.

The Winter patent application EP-A-0 239 400 (herein incorporated by reference) discloses the preparation of an altered, derivative antibody by replacing the complementarity determining regions (CDRs) of a variable region of an immunoglobulin with the CDRs from an immunoglobulin of different specificity, using recombinant DNA techniques ("CDR-grafting"). Thus, CDR-grafting enables "humanization" of antibodies, in combination with the alteration of the framework regions. The manipulation and/or alteration of any given antibody, or gene(s) encoding for the same, to generate a derivative antibody is well known to the art.

The invention will be further described by the following examples.

EXAMPLE 1

Cloning of the TIEF-1 Gene

In order to more fully understand the mechanism by which TIEF-1 influences cell growth and differentiation, TIEF-1 cDNAs were generated by the differential display PCR technique described by Liang et al. (Science, 257, 967 (1992) and *Nucl. Acids Res.*, 21, 3269 (1993)).
Materials and Methods Cell Culture and RNA isolation. The immortalized human fetal osteoblastic (hFOB) cell line, hFOB 1.19, is described by Harris et al. (*J. Bone Miner. Res.*, 10, 178 (1995)). The hFOB cells were routinely grown in DMEM:F12 (1:1) with 10% FBS serum containing media. Cells were plated onto 100 mm culture dishes and allowed to grow to near confluency. At this time, the cells were washed twice with serum-free media and incubated in 10 ml of 1% serum containing media for 48 hours. Serum starved control cells were treated with 0.25% bovine serum albumin (BSA) in phosphate-buffered saline (PBS). Other cultures of serum starved cells were treated with TGF-$\beta_1$ (2 ng/ml) for different time periods and the cells were processed for total RNA isolation using the guanidinium/cesium chloride method of Chirgwin et al. (*Biochemistry*, 18, 5294 (1979)).

Primary cultures of normal adult human osteoblasts (hOB) were grown in culture as described above and the cells were treated with TGF-$\beta_1$ for various time periods and Northern analyses were performed as described below.

Northern blot analysis. Northern blot analysis was performed essentially as described in Subramaniam et al., *J. Cell. Biochem.*, 57, 52 (1995). Briefly, 8 to 15 µg of total RNA preparations were denatured and resolved in a 1% glyoxal agarose gel during electrophoresis. The RNAs were transferred overnight to a Magna 66 nylon membrane (MSI, Fischer Scientific, Pittsburgh, Pa.) by capillary action in 20×SSC (3 M NaCl, 0.3 M trisodium citrate, pH 7.0). The filters were baked for 2 hours at 80° C., hybridized with a [$^{32}$P]-labeled probe, and the blots washed as previously described (Lau et al., *Proc. Natl. Acad. Sci. USA*, 88, 829 (1991)). The probes were labeled with $^{32}$P by random primer extension using the Multiprime DNA labeling system (NEN Research Products, Boston, Mass.). [$\alpha$-$^{32}$P]dCTP with a specific activity of approximately 3000 Ci/mmol (NEN Research Products, Boston, Mass.) was used radiolabel the DNA probes to achieve specific activities of approximately $10^9$ cpm/mg.

Differential Display PCR. Differential display PCR (Liang and Pardee and Liang et al. (both cited supra)) was performed following the manufacturer's protocol (GenHunter kit, Brookline, Mass.). Total RNA was isolated from hFOB 1.19 cells that had been treated with either vehicle (0.25% BSA in PBS) or $10^{-8}$ M TGF-$\beta_1$ for 60 minutes using the guanidinium/cesium chloride method of Chirgwin et al. (cited supra). Total RNA was treated with RNAse-free DNAse to remove any DNA contamination. DNA-free RNA (0.2 µg) from control and TGF-$\beta_1$-treated cells was used as a template for first strand cDNA synthesis in the presence of 10 µM $T_{12}$ MG, $T_{12}$ MC, $T_{12}$ MA, and $T_{12}$ MT primers (GenHunter kit, Brookline, Mass.), MMLV-reverse transcriptase, reverse transcriptase buffer, and 250 µM dNTP mix. $T_{12}$ MG, $T_{12}$ MC, $T_{12}$ MA, $T_{12}$ MT, and $T_{12}$ MN are degenerate anchored oligo-dT primers. For example, $T_{12}$ MA has twelve dT nucleotides followed by either a dG, dA or dC nucleotide which is followed by a dA nucleotide. $T_{12}$ MN has twelve dT nucleotides followed by either a dG, dA or dC nucleotide followed by any of the four deoxyribonucleotides. The synthesized first stand cDNA was used as a template in the next PCR reaction.

In a 0.5 ml microfuge tube the following were added: 2 µl of 10×PCR buffer (50 mM KCl, 1.5 mM MgCl$_2$, 10 mM Tris-HCl, pH 8.3), dNTP mix (25 µM), 5'-random primer (2 µM) or alternatively the primer 5'-CCTGTAATCC-3' (SEQ ID NO: 3), $T_{12}$ MN mix (the same used in the cDNA synthesis described above), 1 µCi of dCTP (3000 Ci/mmol), 2 µl of template cDNA and 1 unit of Taq DNA polymerase (Perkin Elmer). PCR was performed as follows: 94° C., 30 seconds; 40° C., 2 minutes; 72° C., 30 seconds; for 40 cycles. After the PCR was completed, 6 µl of the sample was run on a 6% urea:acrylamide sequencing gel. The dried gel was exposed to an x-ray film and the autoradiogram was analyzed for the differentially expressed genes. As used herein, the term "differentially expressed" means that the expression of a particular RNA molecule is increased or decreased in a culture of cells as a result of exposure of that culture to an agent, e.g., a growth or differentiation-inducing factor, relative to a culture not exposed to the agent. After identifying a differentially expressed band from the autoradiogram of ca. 350 bp in size, the gel was superimposed over the autoradiogram and the band was cut out.

The DNA in the band was then eluted from the gel by soaking the gel in a 100 μl of TE buffer for 10 minutes and then boiling the gel in TE buffer for 10 minutes. The DNA was precipitated using glycogen and ethanol. The precipitated DNA was dissolved in a small volume of $dH_2O$). A portion of this DNA was used as a template in the second PCR along with the same 5' and 3' primers used in the first PCR. The amplified DNA obtained was analyzed in a 1.5% agarose gel. Once the DNA was found to be pure, i.e., without any other contaminating DNA bands, dNTPs and proteins were removed. This DNA was then used as a probe in Northern analyses and cDNA library screening.

cDNA Library Screening. To obtain the full length TIEF-1 cDNA, a hOB cDNA library was screened using the 350 bp DNA fragment described above which represents the 3'-end of the TIEF-1 cDNA. The hOB cDNA library was kindly provided by Dr. Marian Young at the National Institutes of Health. The cDNA library was constructed using poly $A^+$ RNA obtained from a 55 year-old female who had hip replacement surgery. Using the 350 bp DNA as a probe, ~200,000–400,000 plaques were screened. In the primary screen, three positive clones were obtained. The three clones were plated for a secondary screen, but only one of the clones was a potential positive clone. The tertiary screen confirmed this, since 100% of the plaques were positive.

Since the cDNA library was constructed in a lambda ZAPII vector, a pBluescript plasmid containing the insert could be obtained by the in vivo excision of the plasmid from lambda ZAPII vector. The pBluescript plasmid containing the insert was digested with EcoRI to liberate the cDNA insert from the vector. A 2.9 kb insert was obtained. Both strands of the 2.9 kb cDNA were then completely sequenced using a PCR-based sequencing kit and an automated sequencer. There was perfect homology between the 350 bp DNA fragment obtained after differential display PCR and the 3'-end of the 2.9 kb cDNA. The 2.9 kb DNA sequence was analyzed for homologies with known genes in the Genbank using University of Wisconsin GCG Program Fast A.

Results

When differential display PCR was performed from hFOB cell RNA, a 350 bp TGF-β inducible early gene cDNA fragment (350 bp TIEF-1 cDNA) was highly expressed in hFOB cells which were treated with TGF-β for 60 minutes compared to control (untreated) cells. The cDNA fragment was purifed from a gel and used as a probe for Northern analyses.

RNA was isolated from hFOB cells, treated with TGF-$β_1$ for various time periods, fractionated on glyoxal agarose gels, and probed with the 350 bp TIEF-1 cDNA. The differentially expressed TIEF-1 mRNA was minimally detectable in control (vehicle treated) cells, but a rapid and transient increase was observed at 30 minutes after addition of TGF-$β_1$. There was a maximal (greater than 10-fold above control) level of expression measured at two hours posttreatment. The steady-state levels of this 3.5 kb mRNA returned to control levels following three hours of TGF-$β_1$ treatment.

To obtain the full length cDNA, a normal human osteoblast-like cell cDNA library was screened using the 350 bp TIEF-1 cDNA. The library screening resulted in the isolation of a 2.9 kb cDNA encoding a 480 amino acid residue protein, having a long 3'-untranslated region. The cDNA sequence (SEQ ID NO:1) and predicted amino acid sequence (SEQ ID NO:2) are shown in FIG. 1. The amino acid sequences in TIEF-1 which contain the highly conserved zinc finger motifs, as well as other conserved amino acid residues, are shown in FIG. 2.

The cDNA sequence analyses of TIEF-1 indicated that this gene contains three zinc finger motifs at the C-terminal region of the protein. This region of the protein is homologous to zinc finger-containing transcription factors like Sp1, Sp3, Wilm's tumor protein, GT box binding protein, and other zinc finger proteins. In contrast, the N-terminal region of the protein was found to be unique showing no homology to any genes in the Genbank. The zinc finger containing domains were first identified in Xenopus transcription factor TFIIIA (Miller et al., *EMBO J.*, 4, 1609 (1985)) and are known to bind nucleic acid (reviewed in Klug et al., *TIBS*, 12, 464 (1987); Berg, *Proc. Natl. Acad. Sci. USA*, 85, 99 (1988)).

The transcription factor CTF/NF-1 is known to contain proline-rich domains in the C-terminal region which are responsible for a transcriptional activating function (Mermod et al., *Cell*, 58, 741 (1989)). Interestingly, the C-terminal region of TIEF-1 contains a similar proline-rich region (24% proline residues within 125 amino acids) analogous to that of CTF/NF-1 transcription factors. Proline-rich regions are known to bind Src homology-3 (SH3) domains (Ren et al., *Science*, 259, 1157 (1993)). Yu et al. (*Cell*, 76, 933 (1994)) have reported a proline motif of PXXP that can bind SH3 domains which are highly conserved among numerous proteins. The C-terminal region of TIEF-1 contains four PXXP motifs. These proline motifs in TIEF-1 may associate with SH3 domains of src tyrosine kinases which may be involved in the signal transduction processes.

A DNA probe containing TIEF-1 cDNA sequence from 231 to 1509 was amplified using high fidelity Taq polymerase and used to screen a human PAC (phage artificial chromosome) genomic library derived from male white blood cells. One clone (10421) hybridized to the TIEF-1 probe. Southern blot analysis of purified 10421 DNA digested with BamH1, EcoR1, or BamH1/EcoR1 revealed one hybridizing band in each lane. A 10 kilobase EcoR1 fragment was subcloned into pcDNA3 (clone #15) and sequenced for exon/intron boundaries. The sequence analysis revealed that clone #15 contains 4 exons and 3 introns.

EXAMPLE 2

Expression Analyses of the TIEF-1 Gene

To determine whether TIEF-1 is expressed during embryogenesis, the cDNA for human TIEF-1 was labeled and used to probe a mouse embryo tissue Northern blot. A single band of the expected size (3.5 kb) was detected in the mouse, with strong expression in the day 7 embryo, and minimal expression in later stages of fetal development (days 11, 15 and 17). However, TIEF mRNA levels rise again later in certain adult mouse tissues, with the highest expression in skeletal muscle.

hFOB cells were treated with TGF-$β_1$, as described above, together with the protein synthesis inhibitor, cycloheximide (10 μg/ml for two hours), and Northern blot analyses performed using the labeled full length cDNA. A super-induction of TIEF-1 mRNA was observed at two hours post-treatment. This strongly suggests that the increase in TIEF-1 mRNA in hFOB by TGF-β is a primary response and is independent of new protein synthesis. The control of TIEF-1 mRNA expression could also be under the negative control of a protein repressor.

It is also possible that cycloheximide inhibits nucleases that are involved in degradation of TIEF-1 mRNA. This possibility is supported by the fact that TIEF-1 mRNA contains three AUUUA motifs in the 3'-untranslated region of TIEF-1, motifs which are found in c-fos and c-myc nuclear proto-oncogene mRNAs. This motif is a signal for rapid mRNA degradation (Schiavi et al., *Biochimica et Biophysica Acta,* 1114, 95 (1992)). The TIEF-1 mRNA returns to near control levels at 3–4 hours after the addition of TGF-β.

When the RNA synthesis inhibitor actinomycin-D (1 μg/ml), was included with TGF-β for the same period of time, the increase in TIEF-1 mRNA was inhibited. These results suggest that the induction of TIEF-1 mRNA by TGF-β is mediated, at least in part, at the level of transcription. In fact, nuclear run-on transcriptional analysis indicates that the TGF-β regulation of TIEF-1 expression occurs at the level of transcription. Thus, the regulation of the TIEF-1 gene occurs as early as 30 minutes after TGF-β treatment and is independent of new protein synthesis.

hFOB cells were treated with TGF-$β_1$, TGF-$β_2$, and TGF-$β_3$ to determine whether different isoforms of TGF-β have differential effects on TIEF-1 gene expression in osteoblasts. Northern blot analysis showed that all isoforms produced similar responses in TIEF-1 mRNA levels. These results indicate that the different isoforms of TGF-β displayed the same effect on the expression of the TIEF-1 gene.

To determine whether TIEF-1 expression is regulated by TGF-β in normal adult osteoblastic cells, hOB cells were treated for various time periods and Northern blot analyses performed. These data show that a progressive increase in TIEF-1 mRNA was observed with a maximal increase at 1–2 hours of TGF-β treatment.

Transformed human osteosarcoma cells, U2 and MG-63 cells, were also treated with TGF-β for various intervals and total RNA analyzed by Northern blot analysis. A chronological increase in TIEF-1 mRNA was observed with a maximal increase at 1–2 hours of treatment. Thus, TGF-β increased TIEF-1 mRNA in both normal and transformed osteoblasts.

To determine whether other members of TGF-β superfamily have any effect on TIEF-1 mRNA levels, hFOB cells were treated with bone morphogenetic protein-2 (BMP-2) at a concentration of 100 ng/ml for various time periods, and analyzed by Northern blot. The blot shows that the TIEF-1 mRNA levels increased at 1–2 hours of BMP-2 treatment. The bone cells treated with BMP-2 showed the same level of induction of TIEF-1 as seen in the TGF-β treated cells. In contrast, BMP-6 showed low levels, or no, induction of TIEF-1 levels at 100 ng, or 50 ng, of BMP-6, respectively (FIG. 3). Evidence suggests that the BMPs are regulators of mesenchymal cell commitment and differentiation, and that BMP-2 and BMP-6 display a differential pattern of expression during development.

To determine if the induction of TIEF-1 mRNA in hFOB cells is specific to the TGF-β family of growth factors, cells were treated with different growth factors and cytokines, such as TGF-$β_1$ (2 ng/ml), EGF (20 ng/ml), TFN-α (10 U/ml), IL-6 (10 ng/ml), IL-1β (10 U/ml), IGF-1 (3.5 ng/ml), IGF-II (3.5 ng/ml), PDGF 5 ng/ml), and FGF (10 ng/ml). Total RNA was isolated from vehicle-treated (0.25% BSA in PBS for 90 minutes) and growth factor-treated cells and 10 μg of the total RNA was used for Northern blot analysis. The blots were probed for TIEF-1 mRNA and 18 S rRNA. It is evident that TGF-β is the major inducer of TIEF-1 mRNA levels, with a lesser effect by EGF. The remaining growth factors/cytokines had only a minimal effect on TIEF-1 expression.

TIEF-1 mRNA is also induced by 50 ng/ml activin, although reduced levels of TIEF-1 mRNA were observed with higher activin concentrations (200 ng/ml). Treatment with activin did not result in the same level of upregulation of TIEF-1 seen with TGF-β treatment.

In summary, interestingly, in human osteoblasts, the induction of TIEF-1 is unique, as it is growth factor/cytokine specific, e.g., EGF and BMP-2, and to a lesser extent BMP-6, induce the expression of this gene, while the IGFs, several ILs, PDGF, EGF, TNF-α, etc., do not alter the expression.

To investigate whether TIEF-1 expression is specific to osteoblasts or is expressed in other human tissues, multi-tissue Northern blot analysis was performed. The Northern blot contained an equal amount of poly $A^+RNA$ (2 μg) or total RNA (20 μg) from different human tissues which was normalized to β-actin (for polyA+) or GAPDH (for total) mRNA levels. The blot was probed with TIEF-1 cDNA. Normal whole tissue of bone, breast, colon, heart, placenta, endometrium and muscle had high to moderate levels of TIEF-1 expression relative to β-actin or GAPDH. Other tissues, e.g., brain, pancreas, lung, and kidney had no detectable levels of the TIEF-1 mRNA. As expected, both heart and skeletal muscle showed expression of α-actin mRNA in addition to β-actin.

The TIEF-1 cDNA (sense orientation) was cloned into an eukaryotic expression vector and the vector introduced into hFOB cells by electroporation. Stable transfectants resulted in an overproduction of TIEF-1 mRNA and protein. Moreover, these transfectants exhibited a loss of contact inhibition and a loss of anchorage dependency.

The tumorigenic capacity of the TIEF-1 transfectants were tested in nude mice and no tumors were detected by palpation. After 7 weeks the mice were sacrificed and no cancers were found. In vitro proliferation studies conducted at permissive (34° C.) and restrictive (39.5° C.) temperatures indicated reduced $^3$H-thymidine incorporation in these cells compared to control FOB cells. The activity of alkaline phosphatase, a marker of osteoblast phenotype and differentiation, was measured in TIEF-1 sense FOB cells and FOB cells to determine if TIEF-1 alters osteoblast function and differentiation. Alkaline phosphatase activity was decreased in TIEF-1 sense FOB cells compared to FOB control (448±99 versus 1,100±126 nmol AP/mg protein). Thus, FOB cells stably transfected with TIEF-1 were able to proliferate at confluency and in soft agar, but were not tumorigenic. Both cell proliferation and alkaline phosphatase activity were reduced in these cells. Thus, TIEF-1 resembles a nuclear proto-oncogene.

EXAMPLE 3

TIEF-1 Expression is Induced by Estrogen in Normal Cells and is Reduced in Neoplastic Tissue The TIEF-1 gene was localized to human chromosome, band 8q23. Bands q22–24 are frequently altered in several cancers, including those in breast and bone cancers (Isola et al., *Am. J. Pathol.,* 147, 905 (1995); Hecht et al., *Am. J. Hum. Genet.,* 56, 1125 (1995); Raskind et al., *Am. J. Hum. Genet.,* 56, 1132 (1995)).

The expression of TIEF-1 in a human fetal osteoblastic cell line which expresses high levels of the estrogen receptor (ER) (FOB-ER) (Harris et al., *J. Bone Miner. Res.*, 10, 178 (1995); Harris et al., *J. Cell Biochem.*, 59, 193 (1995)) was examined. Subconfluent FOB/ER9 cells were pretreated with 10 nM ICI 182,780 and serum starved for 48 hours prior to treatment with 17-β-esradiol (E2). Cells were treated with 10 nM E2, or the equivalent volume of ethanol evaporated to dryness, and total RNA isolated. The mRNA levels for TIEF-1 were normalized to the levels of GAPDH. Steady-state mRNA levels for TIEF-1 in these cells were rapidly and transiently increased after estrogen (E) treatment, reaching maximal levels within 2 hours with a 3–5-fold induction. This increase was dose-dependent, with maximal stimulation at 10 nM E.

Figure 5:
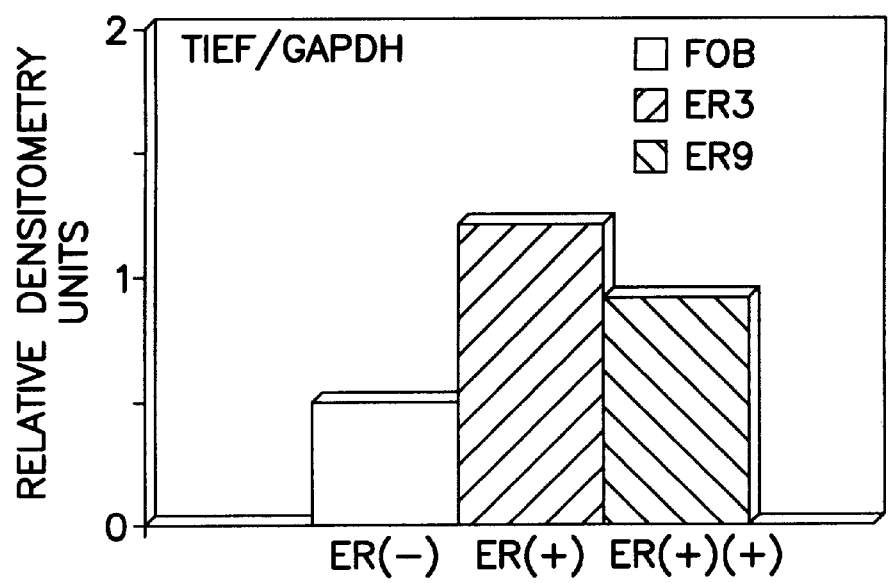
FIG. 5. Basal levels of TIEF-1 expression correlate with the presence of ER. Total RNA was obtained from confluent cultures of FOB, FOB-ER3 (FOB cells stably transformed with the human ER, clone 3) and FOB-ER9 cells (FOB cells stably transformed with the human ER, clone 9) and 10 μg of each sample was analyzed for TIEF-1 and GAPDH mRNA levels. Densitometric analysis of the autoradiographs was performed and the TIEF-1 RNA levels were normalized to the GAPDH levels.

To determine whether TIEF-1 mRNA induction was ER-dependent, ER+ and ER− cell lines were exposed to E and the amount of TIEF-1 mRNA determined. The results showed that TIEF-1 mRNA was induced by E in an ER+ breast cancer cell line, MCF7 (FIG. 4), although with a slightly different temporal pattern than observed in FOB-ER9 cells. The E induction of TIEF-1 was dependent upon the presence of ER since E upregulation of TIEF-1 mRNA was not observed in ER(−) FOB cells, although the FOB-ER cells, which contain functional ER, showed significant TIEF-1 expression (FIG. 5).

Polyclonal antibodies (PAbs) which are highly specific for TIEF-1 were isolated in order to examine TIEF-1 protein expression in tissues. The polyclonal antibodies were generated using synthetic peptides derived from in vitro translated TIEF-1 RNA. Peptides spanning amino acid residues 20–29 (SEQ ID NO:4) and 134–154 (SEQ ID NO:5) in the N-terminal region of TIEF-1 were synthesized, conjugated to KLH, and the conjugate injected into rabbits.

Sera sequentially collected from immunized animals showed significant specific immunoreactivity against TIEF-1 as assayed by ELISA utilizing a recombinant TIEF-1-maltose binding protein (MBP) fusion protein as the positive antigen and MBP as the negative antigen. Affinity-purified sera to peptide 134–154 immunoprecipitated in vitro translated TIEF-1 protein which migrates as a 57 kD band by SDS-PAGE. This sera also immunoprecipitated a specific 57 kD protein that is upregulated by TGF-β treatment of hFOB cells. Affinity-purified sera to peptide 20–29 specifically recognized the TIEF-1-MBP fusion protein as assayed by ELISA. A single band was identified by Western blot analysis of cell extracts with these PAbs.

To identify TIEF-1 polypeptide in tissue samples, a peroxidase avidin-biotin complex (ABC) technique using monoclonal or polyclonal antibodies is employed. Five micron paraffin tissue sections are mounted on aminoalkylsilane-treated glass slides. Heat-induced antigen retrieval is performed by steam treatment of deparaffinized sections in 10 mM citrate buffer, pH 6.0. Endogenous peroxidase activity is blocked by incubation in hydrogen peroxide/methanol. The immunohistochemical technique involves sequential application of 1) appropriately diluted primary antibody; 2) a cocktail of biotinylated goat anti-rabbit and anti-mouse IgG; and 3) peroxidase-conjugated ABC. The antigens are visualized by incubation of sections with either aminoethylcarbazole (membrane and cytoplasmic antigens) or diaminobenzidine (nuclear antigens) in the presence of hydrogen peroxide. Sections are counterstained with a light hematoxylin, and stained slides are mounted with a coverslip. Negative control serial sections for each tissue sample are incubated with nonimmune rabbit or nonimmune mouse IgG in place of specific antibody. Stained sections are scored for intensity of staining on a 0 (negative) to 3+ (intense) scale and for percentage of cells stained (A=<20%, B=20–60%, and C=>60%).

Immunohistochemistry showed that TIEF-1 was a cyto-nuclear protein expressed in only certain cell types in the placenta, pancreas, bone and brain (cerebellum) but not in any cell types of the kidney or muscle. The TIEF-1 protein was localized in the nuclei of some pancreatic cells and brain glial cells, but is found in the cytoplasm in other cells of these organs.

In normal breast and uterine tissues, immunochemical analyses identified TIEF-1 protein only in epithelial cells, which are ER+, but not in stromal cells, which are largely ER−. These data indicated that detectable basal TIEF-1 expression may reflect the presence of ER. Moreover, because TIEF-1 is induced by E, TIEF-1 mRNA and protein levels may serve as a marker for ER levels and possibly E responsiveness in breast cancer. Furthermore, since 80% of all breast cancers that metastasize to bone are ER positive, the levels of TIEF-1 expression may predict metastatic potential, which is a major morbidity factor in breast cancer.

Figure 6:
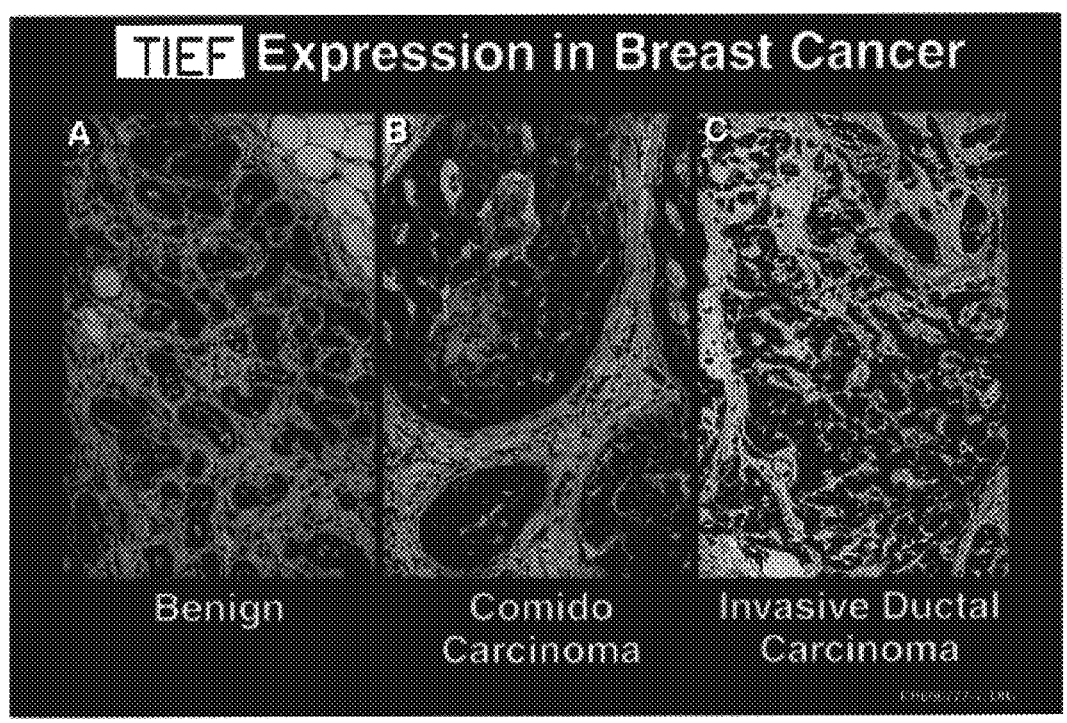
FIG. 6. Immunohistochemical localization of TIEF-1 in breast tissue from different stages of breast cancer: (A) benign breast tissue, (B) breast tissue from a comido carcinoma, and (C) breast tissue from an invasive carcinoma.

Using archival normal and breast cancer specimens, high levels of TIEF-1 protein were found in the perinuclear regions of the epithelial cells of normal breast tissue (FIG. 6A). In the in situ carcinomas (Stage II/III), however, TIEF-1 protein was markedly reduced (FIG. 6B). At this stage of the disease, the number of epithelial cells lining the ducts have greatly increased in number. In invasive carcinoma (Stage IV), in the epithelial cells which have become invasive, TIEF-1 was completely absent (undetectable) (FIG. 6C). These results suggest that the TIEF-1 gene is a tumor suppressor gene in breast epithelial cells.

To further assess whether there is a correlation between TIEF-1 expression and estrogen receptor (ER) status, histological status, chromosomal abnormalities, and tumor progression in breast cancer patients, archival tissue from a cohort of 361 women with resected node-positive breast cancer in clinical trials for systemic adjuvant therapy are analyzed. The cohort is also characterized by DNA flow cytometry for ploidy and s-phase, c-erbB2 expression, p53 gene expression, dextran-coated charcoal and immunohistochemical staining with monoclonal antibody ER1D5.

TIEF-1 expression in these samples is evaluated by Northern blot analysis, Western blot analysis and immunohistochemistry. Northern blot analysis is employed to measure TIEF-1 mRNA levels and TIEF-1 mRNA size in fresh breast cancer (BC) tissues relative to normal breast tissue.

To determine TIEF-1 protein levels in BC tissues, breast biopsies are lysed and cytosolic and/or nuclear fractions are collected. The amount of protein is quantitated via the Bradford method and equivalent amounts of protein are immunoprecipitated using a TIEF-1 specific antibody, e.g., an antibody to peptide 134–154. The immunocomplexes are pelleted using protein-A sepharose beads, boiled in the presence of SDS sample buffer and resolved by SDS-PAGE. The proteins are transferred to nitrocellulose in electrode buffer which contains 10% (v/v) methanol, 10 mM CAPS, pH 11, at 12 v for 1 hour at room temperature. The membrane is blocked with 5% non-fat milk (w/v, dry) in 1×PBS/0.05% Tween 80 for 1 hour at 37° C. with agitation, and incubated with biotinylated-anti-TIEF-1 antibody overnight at 4° C. The blots are thoroughly washed with PBS/0.05% Tween 80 and reacted to peroxidase-conjugated streptavidin (0.1 U/ml) in PBS/0.05% Tween/2% nonfat milk at room temperature for 2 hours. TIEF-1 protein is detected using the ECL kit (Amersham, Arlington Heights, Ill.).

As immunoblotting is a time- and labor-intensive process, and not as quantitative as ELISAs, a two antibody sandwich ELISA which employs a TIEF-1 specific capture moiety, e.g., anti-TIEF-1 peptide 134–154 antibodies, and a labeled detection moiety, e.g., biotinylated-anti-TIEF-1 peptide 20–29 antibodies, can also be employed to determine TIEF-1 levels in tissue, e.g., biopsy, samples. The protein concentration of the biopsy lysates are quantitated using the Bradford method and equivalent protein amounts assayed. The wells are washed as described and reacted with TMB substrate (Kirkgaard and Perry, Gaithersburg, Md.) for 15 minutes at room temperature. The colorimetric change is read at 450 nm.

Immunocytochemistry of TIEF-1 in patient samples, either fresh/frozen or archival breast cancer specimens, using anti-TIEF-1 antibodies is employed to measure changes in the levels and intracellular localization of TIEF-1.

To evaluate whether genetic rearrangements, amplifications and deletions in the TIEF-1 gene are correlated to breast cancer, patient samples can be analyzed by fluorescent in situ hybridization (FISH) to measure gene amplification, using polymorphic microsatellite markers surrounding the TIEF-1 gene to identify chromosomal deletions, and by PCR amplification of TIEF-1 exons followed by single-stranded conformation polymorphism analyses and direct sequencing to evaluate small deletions or point mutations have occurred. For FISH analyses, a TIEF-1 genomic clone is labeled with a fluorophore and the labelled probe is hybridized to fresh or paraffin-embedded tissues. Dual probe hybridiztions are performed with a control probe (in this case, a probe for the centromere of chromosome 8 using a different fluorophore than that used for the TIEF-1 probe).

Southern blot analysis is also employed to assess whether the TIEF-1 gene is amplified, or has large deletions, in tumor specimens. These blots are also analyzed with HER-2/neu and c-myc probes to assess the potential association of the amplification of these genes with that of TIEF-1.

Thus, the detection of TIEF-1 expression can serve as a useful marker for staging, tumor progression, or ER status or response to estrogen therapy, in breast cancer patients.

The complete disclosure of all patents, patent documents and publications cited herein are incorporated by reference as if individually incorporated. The foregoing detailed description and examples have been given for clarity of understanding only. No unnecessary limitations are to be understood therefrom. The invention is not limited to the exact details shown and described for variations obvious to one skilled in the art will be included within the invention defined by the claims.

What is claimed is:

1. An isolated peptide having an amino acid sequence corresponding to SEQ ID NO:2, SEQ ID NO:4, SEQ ID NO:5, or a variant thereof, which peptide, when administered to an animal, results in the production of antibodies that specifically bind to a polypeptide having an amino acid sequence consisting of SEQ ID NO:2, SEQ ID NO:4, or SEQ ID NO:5.

2. A purified antibody that specifically reacts with the peptide of claim 1.

3. A method for detecting or determining the presence or amount of a mammalian polypeptide having SEQ ID NO:2 in a mammalian physiological sample, comprising:

(a) contacting an amount of purified antibodies which specifically react with the polypeptide with the sample to be tested, for a sufficient time to allow the formation of binary complexes between at least a portion of the antibodies and at least a portion of the polypeptide in said sample; and (b) detecting or determining the presence or amount of said binary complexes.

4. The method of claim 3 wherein the absence or amount of said complexes is indicative of a mammal at risk of, or afflicted with, breast cancer.

5. A diagnostic method for monitoring the progression of breast cancer in a patient, comprising
   (a) contacting an amount of purified antibodies which specifically react with a human polypeptide having SEQ ID NO:2, with a sample comprising said polypeptide obtained from said patient, for a sufficient time to allow the formation of binary complexes between at least a portion of the antibodies and a portion of the polypeptide in said sample;
   (b) detecting or determining the presence or amount of said binary complexes;
   repeating steps (a) and (b) at a point later in time; and
   (d) comparing the result of step (b) with the result of step (c), wherein a decreased amount of said complexes at the later point in time is indicative of the progression of said cancer.

6. A hybridoma cell line producing the antibody of claim 2.

7. The method of claim 3 or 5 wherein complex formation is detected by contacting the complex with a second agent comprising a detectable label or which binds a detectable label, so as to form a detectable ternary complex.

8. The method of claim 4 wherein the absence of complexes is indicative of metastatic breast cancer.

9. The method of claim 4 wherein the presence of complexes is indicative of disease which is responsive to steroid therapy.

* * * * *

UNITED STATES PATENT AND TRADEMARK OFFICE
CERTIFICATE OF CORRECTION

PATENT NO. : 6,207,375 B1
DATED : March 27, 2001
INVENTOR(S) : Subramaniam et al.

It is certified that error appears in the above-identified patent and that said Letters Patent is hereby corrected as shown below:

Column 3,
Line 27, delete "thereof he" and insert -- thereof. The --, therefor.

Column 4,
Line 21, delete "comprise" and insert -- comprises --, therefor.
Line 28, delete "determine" and insert -- determined --, therefor.
Line 64, delete "rearanged" and insert -- rearranged --, therefor.

Column 6,
Line 8, delete "encodig" and insert -- encoding --, therefor.
Lines 40-41, delete "pharmaceuatical" and insert -- pharmaceutical --, therefor.

Column 7,
Line 59, delete "non coding" and insert -- non-coding --, therefor.

Column 8,
Line 57, delete "varants" and insert -- variants --, therefor.

Column 10,
Line 40, delete "untanscribed" and insert -- untranscribed --, therefor.
Line 46, delete "retoviral" and insert -- retroviral --, therefor.

Column 11,
Line 51, delete "Mnanual" and insert Manual --, therefor.

Column 12,
Line 16, delete "express" and insert -- expressed --, therefor.
Line 64, delete "contamimant" and insert -- contaminant --, therefor.
Line 67, delete "anion-change" and insert -- anion-exchange --, therefor.

UNITED STATES PATENT AND TRADEMARK OFFICE
CERTIFICATE OF CORRECTION

PATENT NO. : 6,207,375 B1
DATED : March 27, 2001
INVENTOR(S) : Subramaniam et al.

It is certified that error appears in the above-identified patent and that said Letters Patent is hereby corrected as shown below:

Column 13,
Line 40, delete "acylatng" and insert -- acylating --, therefor.

Column 15,
Line 3, delete "prepared" and insert -- preparing --, therefor.
Line 32, delete "specficities" and insert -- specificities --, therefor.

Column 19,
Line 64, delete "PDGF 5 ng/ml)," and insert -- "PDGF (5 ng/ml), --, therefor.

Column 24,
Line 1, delete "evaluate small" and insert -- evaluate whether small --, therefor.

Signed and Sealed this

Twenty-seventh of November, 2001

Attest:

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO.    : 6,207,375 B1
DATED         : March 27, 2001
INVENTOR(S)   : Subramaniam et al.

It is certified that error appears in the above-identified patent and that said Letters Patent is hereby corrected as shown below:

Column 1,
Line 5, insert --
Statement of Government Rights
The invention was made at least in part with a grant from the Government of the United States of America (grant no. AR41652 from the National Institutes of Health). The Government has certain rights to the invention.--.

Signed and Sealed this

Twenty-first Day of May, 2002

*Attest:*

JAMES E. ROGAN
*Director of the United States Patent and Trademark Office*

*Attesting Officer*

SEQUENCE LISTING

```
<160> NUMBER OF SEQ ID NOS: 13

<210> SEQ ID NO 1
<211> LENGTH: 2881
<212> TYPE: DNA
<213> ORGANISM: Homo sapiens

<400> SEQUENCE: 1
gaattcggca cgagcgcccg tctgtggcca agcagccagc agcctagcag ccagtcagct      60
tgccgccggc ggccaagcag ccaaccatgc tcaacttcgg tgcctctctc cagcagactg     120
cggaggaaag aatggaaatg atttctgaaa ggccaaaaga gagtatgtat tcctggaaca     180
aaactgcaga gaaaagtgat tttgaagctg tagaagcact tatgtcaatg agctgcagtt     240
ggaagtctga ttttaagaaa tacgttgaaa acagacctgt tacaccagta tctgatttgt     300
cagaggaaga gaatctgctt ccgggaacac ctgattttca tacaatccca gcatttgtt      360 tgactccacc ttacagtcct tctgactttg aaccctctca agtgtcaaat ctgatggcac     420
cagcgccatc tactgtacac ttcaagtcac tctcagatac tgccaaacct cacattgccg     480 caccttcaa agaggaagaa aagagcccag tatctgcccc caaactcccc aaagctcagg      540
caacaagtgt gattcgtcat acagctgatg cccagctatg taaccaccag acctgcccaa     600
tgaaagcagc cagcatcctc aactatcaga acaattcttt tagaagaaga acccacctaa     660
atgttgaggc tgcaagaaag aacataccat gtgccgctgt gtcaccaaac agatccaaat     720
gtgagagaaa cacagtggca gatgttgatg agaaagcaag tgctgcactt tatgactttt     780
ctgtgccttc ctcagagacg gtcatctgca ggtctcagcc agccctgtg tccccacaac      840 agaagtcagt gttggtctct ccacctgcag tatctgcagg gggagtgcca cctatgccgg     900
tcatctgcca gatggttccc cttcctgcca acaacctgt tgtgacaaca gtcgttccca      960
gcactcctcc cagccagcca ccagccgttt gccccctgt tgtgttcatg ggcacacaag     1020
tccccaaagg cgctgtcatg tttgtggtac cccagcccgt tgtgcagagt tcaaagcctc    1080
```

```
cggtggtgag cccgaatggc accagactct ctcccattgc ccctgctcct gggttttccc    1140
cttcagcagc aaaagtcact cctcagattg attcatcaag gataaggagt cacatctgta    1200
gccacccagg atgtggcaag acatacttta aaagttccca tctgaaggcc cacacgagga    1260
cgcacacagg agaaaagcct ttcagctgta gctggaaagg ttgtgaaagg aggtttgccc    1320
gttctgatga actgtccaga cacaggcgaa cccacacggg tgagaagaaa tttgcgtgcc    1380
ccatgtgtga ccggcggttc atgaggagtg accatttgac caagcatgcc cggcgccatc    1440
tatcagccaa gaagctacca aactggcaga tggaagtgag caagctaaat gacattgctc    1500
tacctccaac ccctgctccc acacagtgac agaccggaaa gtgaagagtc agaactaact    1560
ttggtctcag cgggagccag tggtgatgta aaaatgcttc cactgcaagt ctgtggcccc    1620
acaacgtggg cttaaagcag aagccccaca gcctggcacg aaggcccgc ctgggttagg      1680 tgactaaaag ggcttcggcc acaggcaggt cacagaaagg caggtttcat ttcttatcac    1740
ataagagaga tgagaaagct tttattcctt tgaatatttt ttgaaggttt cagatgaggt    1800
caacacaggt agcacagatt ttgaatctgt gtgcatattt gttactttac ttttgctgtt    1860
tatacttgag accaactttt caatgtgatt cttctaaagc actggtttca agaatatgga    1920
agctggaagg aaataaacat tacggtacag acatggagat gtaaaatgag tttgtattat    1980
tacaaatatt gtcatctttt tctagagtta tcttctttat tattcctagt ctttccagtc    2040
aacatcgtgg atgtagtgat taaatatatc tagaactatc attttacac tattgtgaat      2100 atttggaatt gaacgactgt atattgctaa gagggcccaa agaattggaa tcctccttaa    2160
tttaattgct ttgaagcata gctacaattt gttttttgcat ttttgttttg aaagtttaac    2220
aaatgactgt atctaggcat ttcattatgc tttgaacttt agtttgcctg cagtttcttg    2280
tgtagatttg aaaattgtat accaatgtgt tttctgtaga ctctaagata cactgcactt    2340
tgtttagaaa aaaactgaa gatgaaatat atattgtaaa gaagggatat taagaatctt      2400
agataacttc ttgaaaaaga tggcttatgt catcagtaaa gtacctttat gttatgagga    2460
tataatgtgt gctttattga attagaaaat tagtgaccat tattcacagg tggacaaatg    2520
ttcgtcctgt taatttatag gagttttttg gggatgtgga ggtagttggg tagaaaaatt    2580
attagaacat tcacttttgt taacagtatt tctcttttat tctgttatat agtggatgat    2640
atacacagtg gcaaaacaaa agtacattgc ttaaaatata tagtgaaaaa tgtcactata    2700
tcttcccatt taacattgtt tttgtatatt gggtgtagat ttctgacatc aaaacttgga    2760
cccttggaaa acaaaagttt taattaaaaa aaatccttgt gacttacaat ttgcacaata    2820
tttcttttgt tgtactttat atcttgttta caataaagaa ttccctttgg caaaaaaaaa    2880
a                                                                    2881
```

<210> SEQ ID NO 2
<211> LENGTH: 480
<212> TYPE: PRT
<213> ORGANISM: Homo sapiens

<400> SEQUENCE: 2

Met Leu Asn Phe Gly Ala Ser Leu Gln Gln Thr Ala Glu Glu Arg Met
 1               5                  10                  15

Glu Met Ile Ser Glu Arg Pro Lys Ser Met Tyr Ser Trp Asn Lys
            20                  25                  30

Thr Ala Glu Lys Ser Asp Phe Glu Ala Val Glu Ala Leu Met Ser Met
        35                  40                  45

```
Ser Cys Ser Trp Lys Ser Asp Phe Lys Lys Tyr Val Glu Asn Arg Pro
 50                  55                  60

Val Thr Pro Val Ser Asp Leu Ser Glu Glu Asn Leu Leu Pro Gly
 65                  70                  75                  80

Thr Pro Asp Phe His Thr Ile Pro Ala Phe Cys Leu Thr Pro Pro Tyr
                     85                  90                  95

Ser Pro Ser Asp Phe Glu Pro Ser Gln Val Ser Asn Leu Met Ala Pro
                100                 105                 110

Ala Pro Ser Thr Val His Phe Lys Ser Leu Ser Asp Thr Ala Lys Pro
                115                 120                 125

His Ile Ala Ala Pro Phe Lys Glu Glu Lys Ser Pro Val Ser Ala
130                 135                 140

Pro Lys Leu Pro Lys Ala Gln Ala Thr Ser Val Ile Arg His Thr Ala
145                 150                 155                 160

Asp Ala Gln Leu Cys Asn His Gln Thr Cys Pro Met Lys Ala Ala Ser
                165                 170                 175

Ile Leu Asn Tyr Gln Asn Asn Ser Phe Arg Arg Thr His Leu Asn
                180                 185                 190

Val Glu Ala Ala Arg Lys Asn Ile Pro Cys Ala Ala Val Ser Pro Asn
                195                 200                 205

Arg Ser Lys Cys Glu Arg Asn Thr Val Ala Asp Val Asp Glu Lys Ala
                210                 215                 220

Ser Ala Ala Leu Tyr Asp Phe Ser Val Pro Ser Ser Glu Thr Val Ile
225                 230                 235                 240

Cys Arg Ser Gln Pro Ala Pro Val Ser Pro Gln Gln Lys Ser Val Leu
                245                 250                 255

Val Ser Pro Pro Ala Val Ser Ala Gly Gly Val Pro Met Pro Val
                260                 265                 270

Ile Cys Gln Met Val Pro Leu Pro Ala Asn Asn Pro Val Val Thr Thr
                275                 280                 285

Val Val Pro Ser Thr Pro Pro Ser Gln Pro Pro Ala Val Cys Pro Pro
290                 295                 300

Val Val Phe Met Gly Thr Gln Val Pro Lys Gly Ala Val Met Phe Val
305                 310                 315                 320

Val Pro Gln Pro Val Val Gln Ser Ser Lys Pro Pro Val Val Ser Pro
                325                 330                 335

Asn Gly Thr Arg Leu Ser Pro Ile Ala Pro Ala Pro Gly Phe Ser Pro
                340                 345                 350

Ser Ala Ala Lys Val Thr Pro Gln Ile Asp Ser Ser Arg Ile Arg Ser
                355                 360                 365

His Ile Cys Ser His Pro Gly Cys Gly Lys Thr Tyr Phe Lys Ser Ser
                370                 375                 380

His Leu Lys Ala His Thr Arg Thr His Thr Gly Glu Lys Pro Phe Ser
385                 390                 395                 400

Cys Ser Trp Lys Gly Cys Glu Arg Arg Phe Ala Arg Ser Asp Glu Leu
                405                 410                 415

Ser Arg His Arg Arg Thr His Thr Gly Glu Lys Lys Phe Ala Cys Pro
                420                 425                 430

Met Cys Asp Arg Arg Phe Met Arg Ser Asp His Leu Thr Lys His Ala
                435                 440                 445

Arg Arg His Leu Ser Ala Lys Lys Leu Pro Asn Trp Gln Met Glu Val
450                 455                 460
```

```
Ser Lys Leu Asn Asp Ile Ala Leu Pro Pro Thr Pro Ala Pro Thr Gln
465                 470                 475                 480
```

<210> SEQ ID NO 3
<211> LENGTH: 10
<212> TYPE: DNA
<213> ORGANISM: Artificial Sequence
<220> FEATURE:
<223> OTHER INFORMATION: A primer

<400> SEQUENCE: 3
cctgtaatcc                                                                       10

<210> SEQ ID NO 4
<211> LENGTH: 10
<212> TYPE: PRT
<213> ORGANISM: Homo sapiens

<400> SEQUENCE: 4

```
Ser Glu Arg Pro Lys Glu Ser Met Tyr Ser
1               5                   10
```

<210> SEQ ID NO 5
<211> LENGTH: 21
<212> TYPE: PRT
<213> ORGANISM: Homo sapiens

<400> SEQUENCE: 5

```
Phe Lys Glu Glu Glu Lys Ser Pro Val Ser Ala Pro Lys Leu Pro Lys
1               5                   10                  15

Ala Gln Ala Thr Ser
            20
```

<210> SEQ ID NO 6
<211> LENGTH: 77
<212> TYPE: PRT
<213> ORGANISM: Homo sapiens

<400> SEQUENCE: 6

```
Cys His Ile Pro Gly Cys Gly Lys Val Tyr Gly Lys Thr Ser His Leu
1               5                   10                  15

Arg Ala His Leu Arg Trp His Ser Gly Glu Arg Pro Phe Val Cys Asn
                20                  25                  30

Trp Met Tyr Cys Gly Lys Arg Phe Thr Arg Ser Asp Glu Leu Gln Arg
            35                  40                  45

His Arg Arg Thr His Thr Gly Glu Lys Phe Val Cys Pro Glu Cys
        50                  55                  60

Ser Lys Arg Phe Met Arg Ser Asp His Leu Ala Lys His
65                  70                  75
```

<210> SEQ ID NO 7
<211> LENGTH: 77
<212> TYPE: PRT
<213> ORGANISM: Homo sapiens

<400> SEQUENCE: 7

```
Cys His Ile Gln Gly Cys Gly Lys Val Tyr Gly Lys Thr Ser His Leu
1               5                   10                  15

Arg Ala His Leu Arg Trp His Thr Gly Glu Arg Pro Phe Met Cys Thr
                20                  25                  30

Trp Ser Tyr Cys Gly Lys Arg Phe Thr Arg Ser Asp Glu Leu Gln Arg
            35                  40                  45
```

```
His Lys Arg Thr His Thr Gly Glu Lys Lys Phe Ala Cys Pro Glu Cys
    50                  55                  60

Pro Lys Arg Phe Met Arg Ser Asp His Leu Ser Lys His
65                  70                  75

<210> SEQ ID NO 8
<211> LENGTH: 77
<212> TYPE: PRT
<213> ORGANISM: Homo sapiens

<400> SEQUENCE: 8

Cys His Ile Glu Gly Cys Gly Lys Val Tyr Gly Lys Thr Ser His Leu
1               5                   10                  15

Arg Ala His Leu Arg Trp His Thr Gly Glu Arg Pro Phe Thr Cys Asn
                20                  25                  30

Trp Met Phe Cys Glu Lys Arg Phe Thr Arg Ser Asp Glu Leu Gln Arg
            35                  40                  45

His Arg Arg Thr His Thr Gly Glu Lys Arg Phe Glu Cys Pro Glu Cys
        50                  55                  60

Ser Lys Arg Phe Met Arg Ser Asp His Leu Ser Lys His
65                  70                  75

<210> SEQ ID NO 9
<211> LENGTH: 77
<212> TYPE: PRT
<213> ORGANISM: Homo sapiens

<400> SEQUENCE: 9

Cys His Ile Gln Gly Cys Gly Lys Val Tyr Gly Lys Thr Ser His Leu
1               5                   10                  15

Arg Ala His Leu Arg Trp His Thr Gly Glu Arg Pro Phe Met Cys Thr
                20                  25                  30

Trp Ser Tyr Cys Gly Lys Arg Phe Thr Arg Ser Asp Glu Leu Gln Arg
            35                  40                  45

His Lys Arg Thr His Thr Gly Glu Lys Lys Phe Ala Cys Pro Glu Cys
        50                  55                  60

Pro Lys Arg Phe Met Arg Ser Asp His Leu Ser Lys His
65                  70                  75

<210> SEQ ID NO 10
<211> LENGTH: 77
<212> TYPE: PRT
<213> ORGANISM: Homo sapiens

<400> SEQUENCE: 10

Cys Asp Tyr Pro Gly Cys Thr Lys Val Tyr Thr Lys Ser Ser His Leu
1               5                   10                  15

Lys Ala His Lys Arg Thr His Thr Gly Glu Lys Pro Trp Lys Cys Thr
                20                  25                  30

Trp Glu Gly Cys Asp Trp Arg Phe Ala Arg Ser Asp Glu Leu Thr Arg
            35                  40                  45

His Tyr Arg Lys His Thr Gly Ala Lys Pro Phe Gln Cys Gly Val Cys
        50                  55                  60

Asn Arg Ser Phe Ser Arg Ser Asp His Leu Ala Leu His
65                  70                  75

<210> SEQ ID NO 11
<211> LENGTH: 77
```

```
<212> TYPE: PRT
<213> ORGANISM: Mus musculus

<400> SEQUENCE: 11

Cys Gly His Glu Gly Cys Gly Lys Ser Tyr Ser Lys Ser Ser His Leu
1               5                   10                  15

Lys Ala His Leu Arg Thr His Thr Gly Glu Lys Pro Tyr Ala Cys Ser
                20                  25                  30

Trp Asp Gly Cys Asp Trp Arg Phe Ala Arg Ser Asp Glu Leu Thr Arg
            35                  40                  45

His Tyr Arg Lys His Thr Gly His Arg Pro Phe Cys Cys Gly Leu Cys
        50                  55                  60

Pro Arg Ala Phe Ser Arg Ser Asp His Leu Ala Leu His
65                  70                  75

<210> SEQ ID NO 12
<211> LENGTH: 77
<212> TYPE: PRT
<213> ORGANISM: Homo sapiens

<400> SEQUENCE: 12

Cys His Ile Pro Asp Cys Gly Lys Thr Phe Arg Lys Thr Ser Leu Leu
1               5                   10                  15

Arg Ala His Val Arg Leu His Thr Gly Glu Arg Pro Phe Val Cys Asn
                20                  25                  30

Trp Phe Phe Cys Gly Lys Arg Phe Thr Arg Ser Asp Glu Leu Gln Arg
            35                  40                  45

His Ala Arg Thr His Thr Gly Asp Lys Arg Phe Glu Cys Ala Gln Cys
        50                  55                  60

Gln Lys Arg Phe Met Arg Ser Asp His Leu Thr Lys His
65                  70                  75

<210> SEQ ID NO 13
<211> LENGTH: 77
<212> TYPE: PRT
<213> ORGANISM: Homo sapiens

<400> SEQUENCE: 13

Cys Ala Tyr Pro Gly Cys Asn Lys Arg Tyr Phe Lys Leu Ser His Leu
1               5                   10                  15

Gln Met His Ser Arg Lys His Thr Gly Glu Lys Pro Tyr Gln Cys Asp
                20                  25                  30

Phe Lys Asp Cys Glu Arg Arg Phe Ser Arg Ser Asp Gln Leu Lys Arg
            35                  40                  45

His Gln Arg Arg His Thr Gly Val Lys Pro Phe Gln Cys Lys Thr Cys
        50                  55                  60

Gln Arg Lys Phe Ser Arg Ser Asp His Leu Lys Thr His
65                  70                  75
```